(12) United States Patent
Testani et al.

(10) Patent No.: US 12,741,092 B2
(45) Date of Patent: Sep. 22, 2026

(54) FLUID THERAPY BASED ON ESTIMATED EXCESS FLUID, AND ASSOCIATED SYSTEMS AND METHODS

(71) Applicant: REPRIEVE CARDIOVASCULAR, INC., Milford, MA (US)

(72) Inventors: Jeffrey Testani, New Haven, CT (US); Andrew Halpert, Brookline, MA (US); Kenneth John Luppi, Tewksbury, MA (US); Antony Jonathan Fields, San Francisco, CA (US); Mark Richard Pacyna, Edina, MN (US); Arslan Mazhar Malik, Plymouth, MN (US)

(73) Assignee: REPRIEVE CARDIOVASCULAR, INC., Milford, MA (US)

( * ) Notice: Subject to any disclaimer, the term of this patent is extended or adjusted under 35 U.S.C. 154(b) by 0 days.

(21) Appl. No.: 17/812,143

(22) Filed: Jul. 12, 2022

(65) Prior Publication Data

US 2023/0010793 A1 Jan. 12, 2023

Related U.S. Application Data

(60) Provisional application No. 63/220,880, filed on Jul. 12, 2021.

(51) Int. Cl.
*A61M 5/172* (2006.01)

(52) U.S. Cl.
CPC .................................. *A61M 5/1723* (2013.01)

(58) Field of Classification Search
CPC .................................................. A61M 5/1723
See application file for complete search history.

(56) References Cited

U.S. PATENT DOCUMENTS 3,954,010 A 5/1976 Hilblom
4,132,644 A 1/1979 Kolberg
(Continued)

FOREIGN PATENT DOCUMENTS

DE 4023336 A1 2/1992
DE 4137075 C2 11/1993
(Continued)

OTHER PUBLICATIONS

Felker DM, Diuretic Therapy for Patients With Heart Failure: JACC State-of-the-Art Review. J Am Coll Cardiol 2020;75:1178-1195 (Year: 2020).*

(Continued)

*Primary Examiner* — Alex M Valvis
*Assistant Examiner* — Grace L Rozanski
(74) *Attorney, Agent, or Firm* — Ashurst Perkins Coie US LLP

(57) ABSTRACT

The present technology includes devices, systems, and method for managing a patient's urine output. In some embodiments, an exemplary method includes receiving an estimated amount of excess fluid for the patient; obtaining a urine output rate of the patient; obtaining a diuretic dosage rate of the patient; obtaining (i) a first input corresponding to a percentage of an actual amount of net fluid loss relative to the estimated amount of excess fluid, and/or (ii) a second input corresponding to an estimated amount of fluid remaining; and based on the first input and/or the second input, providing an output associated with adjusting the fluid therapy. Providing the output can include providing an indication with instructions for increasing the patient's urine output by administering an additional diuretic and/or increasing infusion of hydration fluid to the patient.

11 Claims, 8 Drawing Sheets

(56) References Cited

U.S. PATENT DOCUMENTS 4,146,029 A 3/1979 Ellinwood, Jr.
4,204,957 A 5/1980 Weickhardt
4,216,462 A 8/1980 McGrath et al.
4,229,299 A 10/1980 Savitz et al.
4,261,360 A 4/1981 Perez
4,275,726 A 6/1981 Schael
4,291,692 A 9/1981 Bowman et al.
4,343,316 A 8/1982 Jespersen
4,411,649 A 10/1983 Kamen
4,448,207 A 5/1984 Parrish
4,449,538 A 5/1984 Corbitt et al.
4,504,263 A 3/1985 Steuer et al.
4,658,834 A 4/1987 Blankenship et al.
4,712,567 A 12/1987 Gille et al.
4,728,333 A 3/1988 Masse et al.
4,728,433 A 3/1988 Buck et al.
4,745,929 A 5/1988 Silver
4,813,925 A 3/1989 Anderson, Jr. et al.
4,923,598 A 5/1990 Schal
4,994,026 A 2/1991 Fecondini
5,038,109 A 8/1991 Goble
5,098,379 A 3/1992 Conway et al.
5,176,148 A 1/1993 Wiest et al.
5,179,862 A 1/1993 Lynnworth
5,207,642 A 5/1993 Orkin et al.
5,573,506 A 11/1996 Vasko
5,586,973 A 12/1996 Lemaire et al.
5,709,670 A 1/1998 Vancaillie et al.
5,722,947 A 3/1998 Jeppsson et al.
5,769,087 A 6/1998 Westphal et al.
5,814,009 A 9/1998 Wheatman
5,891,051 A 4/1999 Han et al.
5,910,252 A 6/1999 Truitt et al.
5,916,153 A 6/1999 Rhea, Jr.
5,916,195 A 6/1999 Eshel et al.
5,981,051 A 11/1999 Motegi et al.
5,984,893 A 11/1999 Ward
6,010,454 A 1/2000 Arieff et al.
6,171,253 B1 1/2001 Bullister et al.
6,231,551 B1 5/2001 Barbut
6,272,930 B1 8/2001 Crozafon
6,514,226 B1 2/2003 Levin et al.
6,531,551 B2 3/2003 Ohno et al.
6,537,244 B2 3/2003 Paukovits et al.
6,554,791 B1 4/2003 Cartledge et al.
6,640,649 B1 11/2003 Paz et al.
6,740,072 B2 5/2004 Starkweather et al.
6,752,779 B2 6/2004 Paukovits et al.
6,796,960 B2 9/2004 Cioanta et al.
6,827,702 B2 12/2004 Lebel et al.
6,942,637 B2 9/2005 Cartledge et al.
7,029,456 B2 4/2006 Ware et al.
7,044,002 B2 5/2006 Ericson et al.
7,086,615 B2 8/2006 Joseph
7,137,964 B2 11/2006 Flaherty
7,278,983 B2 10/2007 Ireland et al.
7,727,222 B2 6/2010 Da Silva
7,736,354 B2 6/2010 Gelfand
7,739,921 B1 6/2010 Babcock
7,758,562 B2 7/2010 Gelfand
7,758,563 B2 7/2010 Gelfand
7,837,667 B2 11/2010 Gelfand
7,938,817 B2 5/2011 Gelfand
8,007,460 B2 8/2011 Gelfand
8,075,513 B2 12/2011 Rudko et al.
8,233,957 B2 7/2012 Merz et al.
8,444,623 B2 5/2013 Gelfand
8,556,846 B2 10/2013 O'Mahony et al.
8,714,030 B1 5/2014 Liu
9,526,833 B2 12/2016 Gelfand et al.
10,045,734 B2 8/2018 Da Silva
10,537,281 B2 1/2020 Thompson et al.
10,639,419 B2 5/2020 Halpert
10,881,774 B2 1/2021 Halpert
11,064,939 B2 7/2021 Da Silva
11,357,446 B2 6/2022 Levin et al.
11,633,137 B2 4/2023 Conley et al.
11,696,985 B2 7/2023 Halpert
11,950,925 B2 4/2024 Levin
11,986,302 B2 5/2024 Conley et al.
11,992,332 B2 5/2024 Da Silva
2001/0029340 A1 10/2001 Mault et al.
2002/0025597 A1 2/2002 Matsuda
2002/0072647 A1 6/2002 Schock et al.
2002/0107536 A1 8/2002 Hussein
2002/0151834 A1 10/2002 Utterberg
2002/0161314 A1 10/2002 Sarajarvi
2003/0040700 A1 2/2003 Hickle
2003/0048185 A1 3/2003 Citrenbaum et al.
2003/0048432 A1 3/2003 Jeng et al.
2003/0114786 A1 6/2003 Hiller et al.
2004/0025597 A1 2/2004 Ericson et al.
2004/0059295 A1 3/2004 Cartledge et al.
2004/0073177 A1 4/2004 Hickle
2004/0081585 A1 4/2004 Reid
2004/0087894 A1 5/2004 Flaherty
2004/0122353 A1 6/2004 Shahmirian et al.
2004/0133187 A1 7/2004 Hickle
2004/0163655 A1 8/2004 Gelfand et al.
2004/0167415 A1 8/2004 Gelfand
2004/0167464 A1 8/2004 Ireland et al.
2004/0176703 A1 9/2004 Christensen et al.
2004/0193328 A1 9/2004 Zaitsu et al.
2004/0243075 A1 12/2004 Harvie
2005/0027254 A1 2/2005 Vasko
2005/0065464 A1 3/2005 Talbot et al.
2005/0085760 A1 4/2005 Ware et al.
2005/0119626 A1 6/2005 Rahe-Meyer
2006/0052764 A1 3/2006 Gelfand et al.
2006/0064053 A1 3/2006 Bollish et al.
2006/0100743 A1 5/2006 Townsend et al.
2006/0184084 A1 8/2006 Ware et al.
2006/0235353 A1 10/2006 Gelfand et al.
2006/0253064 A1 11/2006 Gelfand et al.
2006/0270971 A1 11/2006 Gelfand et al.
2007/0055198 A1 3/2007 O'Mahony et al.
2007/0088333 A1 4/2007 Levin et al.
2007/0258838 A1 11/2007 Drake et al.
2008/0027409 A1 1/2008 Rudko et al.
2008/0033394 A1 2/2008 Gelfand et al.
2008/0051764 A1 2/2008 Dent et al.
2008/0171966 A1 7/2008 Rudko et al.
2008/0221512 A1 9/2008 Da Silva et al.
2009/0054745 A1 2/2009 Jennewine
2009/0062730 A1 3/2009 Woo
2010/0133510 A1 6/2010 Kim et al.
2010/0185175 A1 7/2010 Kamen
2010/0280443 A1 11/2010 Gelfand et al.
2010/0280444 A1 11/2010 Gelfand et al.
2010/0286559 A1 11/2010 Paz et al.
2010/0312039 A1 12/2010 Quirico
2011/0046514 A1 2/2011 Greenwald et al.
2011/0046516 A1 2/2011 Paz et al.
2011/0106004 A1 5/2011 Eubanks et al.
2011/0120231 A1 5/2011 Berger
2011/0196304 A1 8/2011 Kramer et al.
2011/0218411 A1 9/2011 Keenan
2011/0288524 A1 11/2011 Gelfand et al.
2012/0078137 A1 3/2012 Mendels
2012/0259308 A1 10/2012 Gelfand
2013/0104667 A1 5/2013 Koyano
2013/0235691 A1 9/2013 Volker
2013/0261412 A1 10/2013 Reed
2013/0267892 A1 10/2013 Woolford
2013/0274705 A1 10/2013 Burnes et al.
2013/0304027 A1 11/2013 Haddad et al.
2014/0031787 A1 1/2014 Burnes et al.
2014/0073973 A1 3/2014 Sexton
2014/0163487 A1 6/2014 Tout et al.
2014/0228755 A1 8/2014 Darrah et al.
2014/0260600 A1 9/2014 Rike
2014/0366641 A1 12/2014 Jedema et al.
2015/0025468 A1 1/2015 Grandolfo
2015/0105694 A1 4/2015 Mahajan

(56) References Cited

U.S. PATENT DOCUMENTS

2015/0204860 A1 7/2015 Chui
2015/0233749 A1 8/2015 Wang et al.
2015/0258277 A1 9/2015 Halpert
2016/0051176 A1 2/2016 Ramos et al.
2016/0051750 A1 2/2016 Tsoukalis
2016/0136356 A1 5/2016 Ribble et al.
2017/0016755 A1 1/2017 Boussange et al.
2017/0052056 A1 2/2017 Yamasaki et al.
2017/0290974 A1 10/2017 Tsoukalis
2018/0071455 A9 3/2018 Halpert
2018/0110455 A1 4/2018 Chang et al.
2018/0177945 A1 6/2018 Sims et al.
2018/0245967 A1 8/2018 Parker et al.
2018/0250461 A1 9/2018 Gura
2018/0280620 A1 10/2018 Reichthalhammer
2019/0001057 A1 1/2019 Tsoukalis
2019/0038833 A1 2/2019 Pirazzoli et al.
2019/0046102 A1 2/2019 Kushnir et al.
2019/0046723 A1* 2/2019 Halpert .................... A61B 5/20
2019/0262532 A1 8/2019 Oh et al.
2019/0321588 A1 10/2019 Burnett
2020/0061273 A1 2/2020 Hogard et al.
2020/0230351 A1* 7/2020 Kelly .................... A61M 25/04
2020/0284234 A1 9/2020 Huberts et al.
2020/0297900 A1 9/2020 Holigan et al.
2020/0324044 A1 10/2020 Gylland et al.
2020/0360604 A1 11/2020 Kolko et al.
2020/0405955 A1 12/2020 Shah et al.
2021/0024536 A1* 1/2021 Bhattacharya ............ A61P 1/16
2021/0077007 A1 3/2021 Jouret et al.
2021/0085853 A1 3/2021 Chen et al.
2021/0128815 A1 5/2021 Byrne et al.
2021/0162188 A1 6/2021 Cui
2021/0169408 A1 6/2021 Levin et al.
2021/0170084 A1 6/2021 Zacharia
2021/0196880 A1 7/2021 O'Mahony et al.
2021/0236727 A1 8/2021 Levin et al.
2021/0244381 A1 8/2021 Sweeney et al.
2021/0260306 A1 8/2021 Gravenstein et al.
2021/0283357 A1 9/2021 Leonard
2021/0298653 A1 9/2021 Woodward et al.
2021/0369959 A1 12/2021 Abal et al.
2022/0152302 A1 5/2022 Halpert
2022/0273213 A1 9/2022 Sokolov
2022/0288362 A1 9/2022 Porter et al.
2022/0296140 A1 9/2022 Nguyen et al.
2022/0296406 A1 9/2022 Keelen
2022/0313158 A1 10/2022 Levin et al.
2022/0330866 A1 10/2022 Conley et al.
2022/0330867 A1 10/2022 Conley et al.
2022/0339622 A1 10/2022 Halpert
2023/0010793 A1 1/2023 Testani
2023/0068431 A1 3/2023 Erbey et al.
2024/0347162 A1 10/2024 Meese et al.

FOREIGN PATENT DOCUMENTS

EP 0258690 3/1998
EP 1986007 10/2008
EP 3278833 2/2018
EP 4108171 12/2022
GB 2560580 9/2018
JP 2008110150 5/2008
JP 2010503515 A 2/2010
JP A-2011-520549 7/2011
JP A-2017-536857 2/2017
KR 10-2022-0035738 3/2022
WO WO-1996016685 6/1996
WO WO-1996028209 9/1996
WO WO-1997016220 5/1997
WO WO-1999006087 2/1999
WO WO-2005102441 11/2005
WO WO-2006041496 4/2006
WO WO-2009029899 3/2009
WO WO-2013154783 10/2013
WO WO-2014022422 2/2014
WO WO-2015142617 9/2015
WO WO-2016103256 6/2016
WO 2018044959 A1 3/2018
WO WO-2018114794 6/2018
WO 2019222485 A2 11/2019
WO WO-2019222485 11/2019
WO WO-2020033752 2/2020
WO 2021205345 A1 10/2021
WO WO-2022219578 10/2022
WO 2022259115 A1 12/2022
WO 2024013731 A1 1/2024

OTHER PUBLICATIONS

International Search Report and Written Opinion mailed Jul. 5, 2022; International Patent Application No. PCT/US2022/073651; 14 pages.
Rosenburg et al., "Combination Therapy with Metolazone and Loop Diuretics in Outpatients with Refractory Heart Failure: An Observational Study and Review of the Literature," Cardiovascular Drugs and Therapy, 19:301-306, 2005.
Phillips et al., "Measurement of sodium ion concentration in undiluted urine with cation-selective polymeric membrane electrodes after the removal of interfering compounds", Talanta, Elsevier, Amsterdam, NL, vol. 74, No. 2, Nov. 15, 2007, pp. 255-264.
U.S. Appl. No. 18/434,540, filed Feb. 6, 2024, Halpert.
U.S. Appl. No. 16/544,975, filed Aug. 20, 2019, Levin.
U.S. Appl. No. 18/595,182, filed Mar. 4, 2024, Levin.
U.S. Appl. No. 18/637,340, filed Apr. 16, 2024, Conley et al..
U.S. Appl. No. 18/641,241, filed Apr. 19, 2024, Da Silva.
"2016 ESC Guidelines for the Diagnosis and Treatment of Acute and Chronic Heart Failure—Web Addenda," European Heart Journal, 17 pages.
Adams et al., "Executive Summary: HFSA 2006 Comprehensive Heart Failure Practice Guideline," Journal of Cardiac Failure, vol. 12, No. 1, 2006, pp. 10-38.
Adaptec Medical Devices, "Ongoing Access To Real-Time And Accurate Monitoring Of Urine Output Could Improve Management Of Critically Ill Patients," Clinical Literature Review, (2016) 8 pages.
Allen et al., "Continuous Versus Bolus Dosing of Furosemide for Patients Hospitalized for Heart Failure," American Journal of Cardiology, 105(12): 1794-1794, 2010.
Baliga, "Diuretic Therapy for Heart Failure Patients," American College of Cardiology, 75:1178-1195, 2020.
Bart et al., "Ultrafiltration in Decompensated Heart Failure With Cardiorenal Syndrome", The New England Journal of Medicine, Dec. 13, 2012, 9 pages, Massachusetts Medical Society.
Bell et al., "Risk of Postoperative Acute Kidney Injury in Patients Undergoing Orthopaedic Surgery—Development and Validation of Risk score and Effect of Acute Kidney Injury on Survival: Observational Cohort Study," BMJ: 2015, 9 pages.
Bouman et al., "Red Blood Cell Transfusion and Furosemide in Cardiac Surgery: Friend and Foe?" The Netherlands Journal of Medicine, Dec. 2012, vol. 70, No. 10, 3 pages.
Brater, "Diuretic Therapy," New England Journal of Medicine, 339:387-395, 1998.
Brezis et al., Hypoxia of the Renal Medulla—Its Implications for Disease, New England Journal of Medicine, vol. 322, No. 10, Mar. 9, 1995, 9 pages.
Briguori et al., "Renal Insufficiency After Contrast Media Administration Trial II (Remedial II): RenalGuard System in High-Risk Patients for Contrast-Induced Acute Kidney Injury", Circulation, Journal of the American Heart Association, Mar. 13, 2011, 10 pages.
Conradds, "Sensitivity And Positive Predictive Value Of Implantable Intrathoracic Impedance Monitoring As A Predictor Of Heart Failure Hospitalizations: The Sense-HF Trial," European Heart Journal (2011) 32, 2266-2273, 8pages.
Cosgrove III et al., "Automated Control Postoperative Hypertension: A Prospective Randomized Multicenter Study," 1989 by The Society of Thoracic Surgeons, 6 pages.

(56) References Cited

OTHER PUBLICATIONS

Dorval et al., "Feasibility Study of the RenalGuard™ Balanced Hydration System: A Novel Strategy for the Prevention of Contrast-Induced Nephropathy in High Risk Patients", International Journal of Cardiology, 2011, 5 pages, Elsevier Ireland Ltd.

Doty et al., Effect of Increased Renal Venous Pressure on Renal Function, The Journal of Trauma: Injury, Infection and Critical Care, vol. 47, No. 6, Dec. 1999, 4 pages.

Edelson et al., Pharmacokinetics of lohexol, a New Nonionic Radiocontrast Agent, in Humans, Journal of Pharmaceutical Sciences, vol. 73, No. 7, Jul. 1984, 3 pages.

Ellison et al., "Diuretic Treatment in Heart Failure," New England Journal of Medicine, 377:1964-1975, 2017.

Farcy, "Review: Pitfalls in Using Central Venous Pressure as a Marker of Fluid Responsiveness," Emergency Medicine. Jan. 2016;48(1):18-28, 15 pages.

Farkas, "Deresuscitation: Dominating the Diuresis," The Internet Book of Critical Care, 43 pages, 2020.

Felker et al., "Diuretic Strategies in Patients With Acute Decompensated Heart Failure", The New England Journal of Medicine, Mar. 3, 2011, vol. 364, No. 9, 9 pages.

Furutani et al., "An Automatic Control System of the Blood Pressure of Patients Under Surgical Operation," International Journal of Control, Automation, and Systems, vol. 2, No. 1, Mar. 2004, pp. 39-54.

Gheorghiade et al., "Current Medical Therapy for Advanced Heart Failure," American Heart Journal, Jun. 1998, pp. S231-S248.

Gloor, James M. and Vincente E. Torres, Reflux and Obstructive Nephropathy, Atlas of Diseases of the Kidney, on-line edition, vol. Two, Section I, Ch. 8, p. 8.1-8.25, 1999, 27 pages.

Goren et al., "Perioperative Acute Kidney Injury," British Journal of Anaesthesia, 2015, 12 pages.

Hasselblad et al., "Relation Between Dose of Loop Diuretics and Outcomes in a Heart Failure Population: Results of the Escape Trial", European Journal of Heart Failure, 9(10): 1064-1069, 2007.

Heyman et al., Pathophysiology of Radiocontrast Nephropathy: A Role for Medullary Hypoxia, Investigative Radiology, vol. 34, No. 11, Nov. 1999, 7 pages.

Hvistendahl et al., Renal Hemodynamic Response to Gradated Ureter Obstruction in the Pig, Nephron 1996, 74:168-74, 7 pages.

Jin et al., "Intensive Monitoring of Urine Output Is Associated With Increased Detection of Acute Kidney Injury and Improved Outcomes," Chest Journal—Original Research Critical Care, 152#5, pp. 972-979 (Nov. 2017) 8 pages.

Josephs et al., "Perioperative Risk Assessment, Prevention, and Treatment of Acute Kidney Injury," International Anesthesiology Clinics, vol. 47, No. 4, www.anesthesiaclinics.com, pp. 89-105.

Kalantari, "Assessment Of Intravascular Volume Status And Volume Responsiveness In Critically Ill Patients," Kidney International (2013) 83, 1017-1028 (Jan. 9, 2013) 12 pages.

Kolh, "Renal Insufficiency After Cardiac Surgery: A Challenging Clinical Problem," European Heart Journal, 2009, pp. 1824-1827.

Lara, "Accurate Monitoring Of Intravascular Fluid Volume: A Novel Application Of Intrathoracic Impedance Measures For The Guidance Of vol. Reduction Therapy," IJC Heart & Vasculature, 8 (2015) pp. 47-51, 5pages.

Lassnigg et al., "Lack of Renoprotective Effects of Dopamine and Furosemide During Cardiac Surgery," J. Am Soc Nephrol, 2000, pp. 97-104.

Lelarge et al., Acute Unilateral Renal Failure and Contralateral Ureteral Obstruction, American Journal of Kidney Diseases, vol. XX, No. 3, Sep. 1992, 3 pages.

Lenihan et al., "Trends in Acute Kidney Injury, Associated Use of Dialysis and Mortality After Cardiac Surgery, 1999 to 2008," Ann Thorac Surg. 2013, 17 pages.

Levin et al. High-volume diuresis with matched maintenance of intravascular vol. may prevent contrast-induced nephropathy in post-transplant patients with moderate-severe baseline renal impairment, Cardiovascular Revascularization Medicine, Elsevier, NL, vol. 8, No. 2, Apr. 1, 2007, 1 page.

Lloyd-Jones et al., "Heart Disease and Stroke Statistics—2009 Update. A Report From the American Heart Association Statistics Committee and Stroke Statistics Subcommittee", Circulation, Journal of the American Heart Association, Jan. 27, 2009, 161 pages.

Magder et al., "The Clinical Role of Central Venous Pressure Measurements", Journal of Intensive Care Medicine 22(1); 207, 8 pages.

Marenzi et al., "Prevention of Contrast Nephropathy by Furosemide With Matched Hydration," JACC: Cardiovascular Interventions, 5(1):90-97, 2011.

Marenzi et al.. "Prevention of Contrast Nephropathy by Furosemide With matched Hydration. The Mythos (Induced Diuresis With Matched Hydration Compared to Standard Hydration for Contrast Induced Nephropathy Prevention) Trial", JACC: Cardiovascular Interventions, vol. 5, No. 1, 2012 The American College of Cardiology Foundation, 8 pages.

Mawer et al., "Value of Forced Diuresis in Acute Barbiturate Poisoning", Jun. 29, 1968, British Medical Journal, 2, 4 pages.

Mayo Clinic, "Creatinine Test", Mayo Foundation for Medical Education and Research (MFMER) (downloaded Aug. 16, 2018).

Meersch et al., "Perioperative Acute Kidney Injury: An Under-Recognized Problem," vol. 125, No. 4, www.anesthesia-analgesia.org, Oct. 2017, pp. 1223-1232.

Mendeley et al., "Furosemide", Science Direct, 5 pages, 2016.

Oh et al., "Loop Diuretics in Clinical Practice," Review: Electrolyte Blood Press, 13(1): 5 pages, 2015.

Oh et al., "Loop Diuretics In Clinical Practice", Electrolytes & Blood Pressure, www.ncbi.nlm.nih.gov/pmc/articles/PMC4520883, printed Mar. 25, 2019, 6 pages.

Olivero et al., "Acute Kidney Injury After Cardiovascular Surgery: An Overview," debakeyheartcenter.com/journal, 2012, pp. 31-36.

Otero, "A New Device to Automate the Monitoring of Critical Patients' Urine Output", Hindawi Publishing Corp, BioMed Research Int'l, vol. 2014, Article ID 587593, 8 pages.

Palazzuli et al. "Continuous versus bolus intermittent loop diuretic infusion in acutely decompensated heart failure: a prospective randomized trial," Critical Care 18, 2014.

Paterna et al., "Changes in Brain Natriuretic Peptide Levels and Bioelectrical Impedance Measurements After Treatment With High-Dose Furosemide and Hypertonic Saline Solution Versus High-Dose Furosemide Alone in Refractory Congestive Heart Failure", Journal of the American College of Cardiology, 2005, vol. 45, No. 12, 7 pages.

Pederson et al., Renal Water and Sodium Handling During Gradated Unilateral Ureter Obstruction, Scand J. Urol Nephrol, 2002, 36:163-72, 11 pages.

Prandota et al., "Pharmacokinetics and metabolism of furosemide in man," European Journal of Drug Metabolism and Pharmcokinetics, 1(4): 5 pages, 1976.

Rihal et al., Incidence and Prognostic Importance of Acute Renal Failure After Percutaneous Coronary Intervention, Circulation, May 14, 2002, 6 pages.

Rosamilia et al., Electromotive Drug Administration of Lidocaine and Dexamethasone Followed by Cystodistension in Women with Interstitial Cystitis, International Urogyecologyl Journal, Pelvic Floor Dysfunction 1997; 8: 142-5, 4 pages.

Rui Geng et al., "Identification of Modifiable Risk Factors for Acute Kidney Injury After Coronary Artery Bypass Graft Surgery in an Asian Population," The Journal of Thoracic and Cardiovascular Surgery, Apr. 2014, pp. 1356-1361.

S215 Ultra Low Profile Single Point Load Cell-Strain Guage Sensors and Load Cells, Ultra-Low Profile Single Point Load Cell-S215, http://smdsensors.com/detail_pgs/s215.htm 2005, 3 pages.

Shepherd, "Measuring and Managing Fluid Balance", Nursing Times, vol. 107, No. 28, pp. 12-16 (Jul. 19, 2011) 5 pages.

Solomon et al., Effects of Saline, Mannitol, and Furosemide on Acute Decreases in Renal Function Induced by Radiocontrast Agents, The New England Journal of Medicine, vol. 331: 1416-1420, Nov. 24, 1994, No. 21, 5 pages.

Stevens, Melissa A., MD et al., A Prospective Randomized Trial of Prevention Measures in Patients at High Risk for Contrast Nephropathy, Results of the P.R.I.N.C.E. Study, Journal of American College of Cardiology, vol. 33, No. 2, Feb. 1999, 9 pages.

(56) References Cited

OTHER PUBLICATIONS

Stevenson et al., "Editorial Comment, Torrent or Torment From the Tubules?", Challenge of the Cardiorenal Connections, Journal of the American College of Cardiology, vol. 45, No. 12, 2005, 4 pages.
Stickler et al., "A Sensor To Detect the Early Stages in the Development of Crystalline Proteus mirabilis Biofilm on Indwelling Bladder Catheters", Journal of Clinical Microbiology, Apr. 2006, p. 1540-1542.
Teixeira et al., "Fluid Balance and Urine Volume are Independent Predictors of Mortality in Acute Kidney Injury", Critical Care 17:R14 (2013) 11 pages.
Testani et al., "Rapid and Highly Accurate Prediction of Poor Loop Diuretic Natriuretic Response in Patients with Heart Failure," Circulation; Heart Failure, vol. 9. No. 1, 2016, 32 pages.
Thakar, "Perioperative Acute Kidney Injury," Advances in Chronic Kidney Disease, vol. 20, No. 1, 2013, pp. 67-75.
Tricoli, "Miniaturized Bio-and Chemical-Sensors for Point-of-Care Monitoring of Chronic Kidney Diseases," Sensors 2018, 18, 942; (Mar. 22, 2018) 18 pages.
Unknown Author, "Furosemide Drug Summary," Prescriber's Digital Reference, pp. 1-31, 2016.
Vellinga et al., "Identification of Modifiable Risk Factors for Acute Kidney Injury After Cardiac Surgery," The Netherlands Journal of Medicine, vol. 70, No. 10, Dec. 2012, pp. 450-454.
Wakelkamp et al., The influence of drug input rate on the development of tolerance to frusemide, Br. J. Clin. Pharmacol 1998, 46:479-487, 9 pages.
Weinstein et al., Potential deleterious Effect of Furosmide in Radiocontrast Nephropathy, Department of Medicine, Hadassah Univeristy Hospital, Mount Scopus, Jerusalem, Israel, Nephron 1992, 62: 413-415, pages.
Yeh et al., "Goal-directed diuresis: A case - control study of continuous furosemide infusion in critically ill trauma patients", The Journal of Emergencies, Trauma, and Shock, 8(1): 34-38, 2015.
Written Opinion of the International Searching Authority for PCT Application No. PCT/US2005/008948 dated Oct. 3, 2006, 3 pages.
Written Opinion of the International Searching Authority for PCT Application No. PCT/US2007/021791 dated May 8, 2008, 7 pages.
Written Opinion of the International Searching Authority for PCT Application No. PCT/U20S07/009685 dated Jul. 18, 2008, 10 pages.
Written Opinion of the International Searching Authority for PCT Application No. PCT/US2007/009684 dated Jul. 21, 2008, 7 pages.
Written Opinion of the International Searching Authority for PCT Application No. PCT/US2008/007845 dated Sep. 17, 2008, 5 pages.
Written Opinion of the International Searching Authority for PCT Application No. PCT/US2008/007841 dated Sep. 18, 2008 4 pages.
Written Opinion of the International Searching Authority for PCT Application No. PCT/US2007/009683 dated Nov. 24, 2008, 6 pages.
Written Opinion of the International Searching Authority for PCT Application No. PCT/US2009/002739 dated Jun. 19, 2009, 4 pages.
Written Opinion of the International Searching Authority for PCT Application No. PCT/US2010/000137 dated Mar. 16, 2010, 8 pages.
Written Opinion of the International Searching Authority for PCT Application No. PCT/US2015/020196, dated Jun. 12, 2015, 5 pages.

* cited by examiner

FLUID THERAPY BASED ON ESTIMATED EXCESS FLUID, AND ASSOCIATED SYSTEMS AND METHODS

CROSS-REFERENCE TO RELATED APPLICATIONS

The present application is related to U.S. patent application Ser. No. 17/112,925, filed Dec. 4, 2020, and claims priority to U.S. Provisional Patent Application No. 63/220,880, filed Jul. 12, 2021, the disclosures of which are each incorporated herein by reference in their entireties.

TECHNICAL FIELD

The present disclosure generally relates to medical devices and, in particular, to systems for providing fluid therapy and associated methods and devices.

BACKGROUND

Human physiological systems seek to naturally maintain a balance between fluid intake and fluid excretion. An imbalance in fluid intake and excretion rates may cause the body to retain excess amounts of fluid, also known as fluid overload. Fluid overload can be caused by acute decompensated heart failure (ADHF), chronic heart failure (CHF), or other conditions in which insufficient fluid is excreted. Patients exhibiting fluid overload may suffer from shortness of breath (dyspnea), edema, hypertension, and other undesirable medical conditions.

To treat fluid overload, patients are typically administered a diuretic drug which induces and/or increases urine production, thus reducing the amount of fluid and sodium in the body. The rate of urine output may be carefully monitored and/or controlled for safety reasons, e.g., to avoid placing undue stress on the patient's kidneys. Different patients may respond differently to treatment, such that the same diuretic type and/or dosage may produce drastically different urine output rates. However, conventional systems and methods for treating fluid overload may not be capable of accurately monitoring a patient's urine output and/or responding to changes in urine output. Additionally, conventional treatment systems and devices may not be capable of inducing high urine production rates. Accordingly, there is a need for improved fluid therapy systems and methods.

BRIEF DESCRIPTION OF THE DRAWINGS

Features, aspects, and advantages of the presently disclosed technology may be better understood with regard to the following drawings.

Figure 1A:
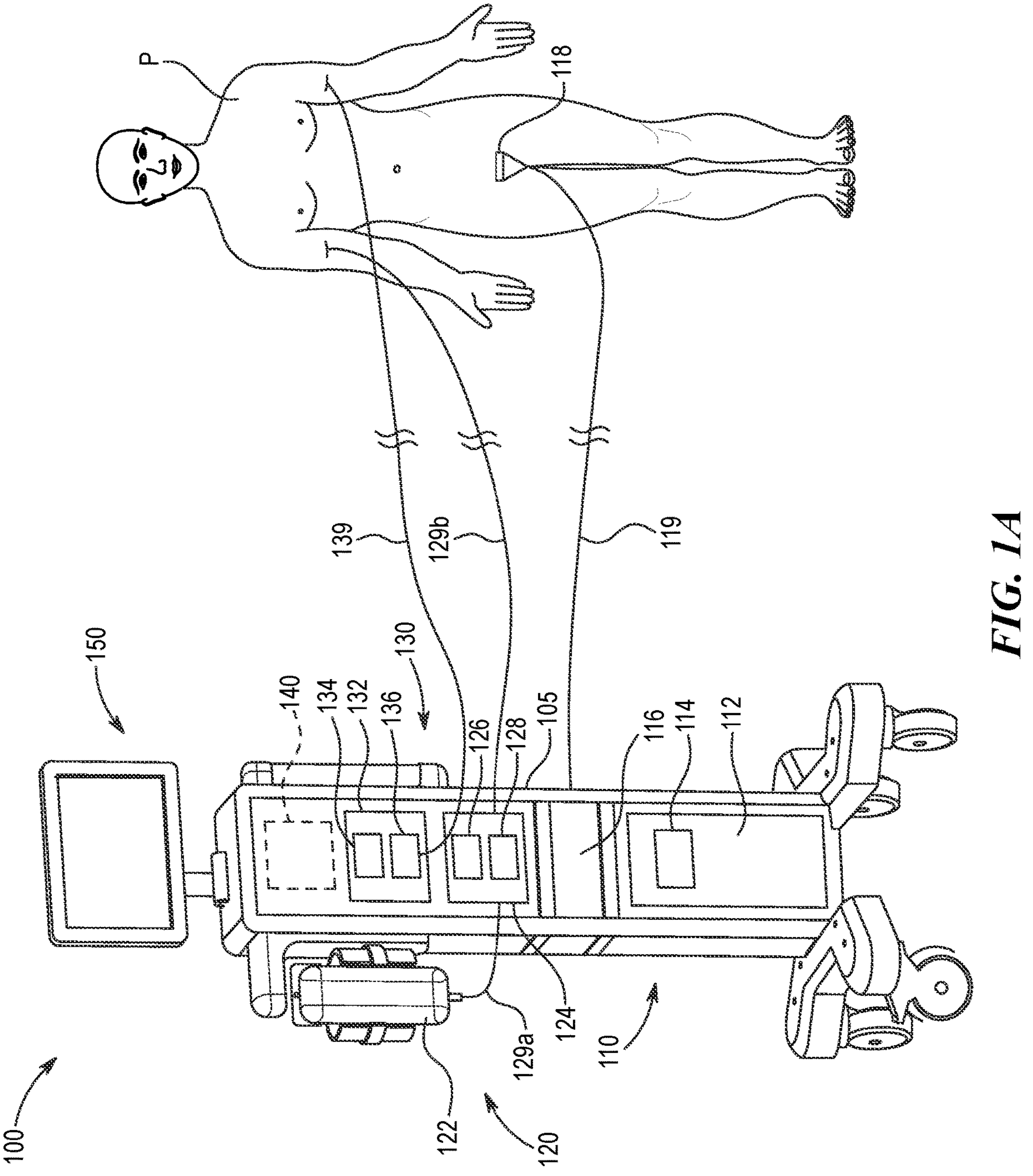
FIGS. 1A and 1B are partially schematic views of fluid management systems configured in accordance with embodiments of the present technology.

A person skilled in the relevant art will understand that the features shown in the drawings are for purposes of illustrations, and variations, including different and/or additional features and arrangements thereof, are possible.

DETAILED DESCRIPTION

The present technology is directed to systems, devices, and/or methods for managing (e.g., increasing or decreasing) a patient's urine output based at least in part on an amount of estimated excess fluid of the patient, and embodiments of the present technology relate to infusing diuretic and/or hydration fluid to increase or optimize urine output from the patient. While a standard treatment protocol can be effective for most patients, some patients can have unique conditions and/or abnormal responses to the standard treatment protocols that prevent or inhibit optimal therapy. As an example, certain patients may not react to some diuretics and/or may have underlying conditions (e.g., low or high blood pressure) which limit their urine output rates, or make treatment to achieve maximum urine output rates more difficult. For such patients, additional steps or protocols may be necessary to increase urine output and relieve fluid overload conditions.

As described herein, embodiments of the present technology can manage a patient's fluid therapy and urine output based on (i) a first input corresponding to a percentage of an actual amount of net fluid loss relative to an estimated amount of excess fluid for the patient (e.g., an estimated amount of the patient's excess fluid remaining and/or to be removed) and/or (ii) a second input corresponding to an estimated amount of excess fluid the patient retains (i.e., remaining in) the patient. If the first input is at or above a predetermined percentage threshold (e.g., 60%, 70%, or 80%) or if the second input is at or below a predetermined fluid threshold (e.g., 0.5 Liters (L), 1.0 L, 1.5 L, or 2 L), then the system may determine that urine output and/or fluid loss for the patient is sufficient and that therapy should be stopped (e.g., automatically stopped) immediately or after a period of time (e.g., one hour). Alternatively, if the first input is below the predetermined percentage threshold and the second input is above the predetermined fluid threshold, then the system may determine that urine output and/or fluid loss is insufficient and can take steps to improve fluid therapy. As a specific example, if less than 80% of the estimated amount of excess fluid has been removed and more than 1 L of fluid remains to be removed from the patient, then the system may take steps to escalate therapy. In such embodiments, the system may provide an output or recommend (e.g., via software, labeling, etc.) infusing a second diuretic, in addition to a first diuretic already being infused, and/or increasing a rate of hydration fluid infusion, both of which are configured to increase net fluid loss from the patient, or other therapy escalations.

In some embodiments, the system may only determine that a patient's urine output is low and/or take actions to increase urine output if certain other conditions are also met. For example, the system may determine whether (i) the urine output rate over a first time period is below a predetermined urine output threshold, and/or (ii) the diuretic dosage rate over a second time period is above a predetermined diuretic threshold. If both conditions are met, meaning the urine output rate is below the predetermined urine output threshold and the diuretic dosage rate is above the predetermined diuretic threshold, then the system may determine whether the patient's fluid therapy should be escalated, e.g., based on the first input and the second input.

In view of the above and as described herein, embodiments of the present technology can advantageously identify whether a patient's urine output is low and take actions (e.g., automatic actions, recommendations, etc.) to improve fluid therapy by escalating therapy in ways designed to increase urine output. More broadly, embodiments of the present technology can manage a patient's urine output by ceasing fluid therapy for instances of sufficient fluid loss and improving fluid therapy by increasing urine output for instances of insufficient fluid loss.

The headings provided herein are for convenience only and are not intended to limit or interpret the scope or meaning of the technology.

I. Fluid Management Systems and Methods

The present technology is generally directed to systems, devices, and associated methods for managing fluid levels of a patient. In some embodiments, the systems, devices, and methods described herein are used to treat a patient for fluid overload. To treat fluid overload, patients can be administered a diuretic drug which induces and/or increases urine production. For example, loop diuretics are diuretics that act at the ascending limb of the loop of Henle in the kidney, and include bumetanide (Bumex®), ethacrynic acid (Edecrin®), furosemide (Lasix®), torsemide (Demadex®), thiazide and thiazide-type diuretics (e.g., chlorothiazide, metolazone), potassium-sparing diuretics (e.g., amiloride, spironolactone), carbonic anhydrase inhibitors (e.g., acetazolamide), and osmotic diuretics (e.g., mannitol). Diuretics can be given orally as a pill or as an intravenous (IV) injection. IV diuretics can be used when oral diuretics are no longer effective and/or able to be absorbed.

The short-term effects of diuretics on a patient's urine production may be difficult to predict, particularly at early stages of treatment. For example, one patient may produce much less urine than expected for a given dose of diuretic, while another patient administered the same dose may produce very large amounts of urine. Low urine production can prolong treatment time and/or reduce treatment efficacy, while high urine production can raise concerns of hypotension, hypovolemia, electrolyte imbalance (e.g., hypokalemia), and/or vital organ damage. High doses of a diuretic, regardless of the urine response, can also raise concerns about ototoxicity. Due to these uncertainties, physicians typically initially prescribe a conservative (e.g., low) diuretic dosage and wait a few hours before considering whether to increase the dosage. If the physician determines that a higher diuretic dosage is needed, the physician may slowly and incrementally increase the dosage until the patient's urine output reaches the desired level and/or rate. However, this approach can prolong the time the patient remains in the fluid overloaded condition, which can exacerbate the patient's underlying clinical state. For example, conservative treatment procedures can require hours or even days before the patient's urine output is sufficiently high to cause significant fluid loss and relieve the fluid overload condition. The patient may be hospitalized for several days (e.g., 4-5 days), which can be expensive and burdensome. Additionally, the long-term treatment efficacy may be limited, such that approximately 25% of patients are readmitted for fluid overload within 30 days.

The effectiveness and safety of fluid therapy can also vary based on patient acuity and the risk of hypotension. For example, patients can be treated via (i) a single loop diuretic, (ii) a combination of a loop diuretic and a thiazide or thiazide-type diuretic, (iii) a combination of a loop diuretic, one or more thiazide diuretics (e.g., metolazone or amiloride), a Potassium-sparing diuretic (e.g., spironolactone, amiloride) a carbonic anhydrase inhibitor (e.g. acetazolamide) and an SGLT2 inhibitor (e.g. Empagliflozin), and (iv) ultrafiltration. Without being bound by theory, this list of treatment options is in order of (i) increasing risk of hypotension and other side effects, and (ii) increasing ceiling of patient acuity for effectiveness, e.g., with a single loop diuretic having the relatively lowest risk of hypotension and other side effects and the relatively lowest ceiling of acuity for effectiveness (e.g. loop diuretics may have limited efficacy in a very sick patient with very poor renal function), and ultrafiltration having the relatively highest risk of hypotension and the relatively highest ceiling of patient acuity for effectiveness (e.g. ultrafiltration removes fluid from patients even with no renal function). Given the desire to minimize the risk of hypotension and other side effects in a context where it is very difficult to accurately access a patient's underlying acuity and diuretic responsiveness, determining and providing the most effective therapy is difficult.

To overcome these and other challenges associated with fluid therapy, the present technology provides systems, devices and methods for managing a patient's fluid levels while reducing the risk of side effects (e.g., the risk of hypotension, etc.). In some embodiments, the present technology can (i) improve efficacy, safety, and quality of fluid management treatment, (ii) improve resource management in hospitals and other clinical settings, (iii) quickly assess if a patient is diuretic resistant, and/or (iv) increase diuretic efficiency (the amount of urine and/or excreted electrolytes (e.g., sodium) obtained over a given time per mg of diuretic infused intravenously). The embodiments described herein can increase net removal of fluid and/or electrolytes (e.g., sodium and/or chloride), and can also treat fluid overload conditions in a more efficient manner (e.g., shorter timeframe and/or higher net fluid loss). In at least some embodiments, the systems, devices, and methods of the present technology can determine whether patient urine output rates and/or net fluid loss is meeting expectations, and if not, make adjustment based on predetermined guidelines to improve net fluid loss. As an example, embodiments of the present technology can adjust or suggest the adjustment of the diuretic (e.g., the type of diuretic, the combination of diuretics, the diuretic dosage rate, etc.) and/or the patient's hydration fluid infusion rate based at least partially on the patient's urine output and/or an amount of estimated of excess fluid to be removed from the patient. Administering a second or different diuretic can improve net fluid loss for a patient that may be diuretic resistant, and thereby mitigate fluid overload conditions. Additionally or alternatively, infusing hydration fluid at increasing rates can replace fluid lost by the patient during therapy and inhibit or prevent the patient from becoming sodium avid, becoming diuretic resistant, and/or from entering a hypotensive state. Accordingly, embodiments of the present technology can deliver improved fluid therapy by enabling patients to receive a wider range of treatment options with a reduced risk of diuretic resistance or hypotension.

FIG. 1A is a partially schematic illustration of a fluid management system 100 ("system 100") for monitoring urine output and/or control fluid infusion into a patient P, in accordance with embodiments of the present technology. The system 100 includes a urine collection and monitoring system 110 ("urine system 110"), an automated hydration fluid infusion system 120 ("hydration system 120"), an automated diuretic infusion system 130 ("diuretic system 130"), a controller or control system 140 ("controller 140"), and a display or input/output unit 150 ("display 150"). The controller 140 can be operably coupled to each of the urine system 110, hydration system 120, diuretic system 130, and/or display 150. The system 100 can further include a console or structure 105 ("console 105") that incorporates, houses, and/or otherwise supports all or portions of the urine system 110, hydration system 120, diuretic system 130, the controller 140, and/or the display 150.

The urine system 110 is configured to collect urine from the patient P and/or monitor the patient's urine output (e.g., urine output amount and/or rates). The urine system 110 can include one or more collection containers 112 ("container 112") configured to hold urine, such as a disposable bag or other collection device. The container 112 can be fluidly coupled to the patient P via a fluid line 119 (e.g., a tubing line). The fluid line 119 can be connectable to a disposable catheter 118 (e.g., a Foley catheter, Texan Condom catheter, PureWick catheter, etc.) placed in or otherwise connected to the bladder of the patient P.

In some embodiments, urine flow through the fluid line 119 is driven by the patient's urine production, gravity (e.g., the bladder of the patient P is positioned higher than the container 112), and/or a siphon effect between the patient's bladder and the container 112. In other embodiments, the urine system 110 can also include a pump (not shown) operably coupled to the fluid line 119 for actuating urine flow through the fluid line 119 and into the container 112. The pump can be or include any device suitable for pumping fluid, such as a peristaltic pump. The pump can be used to initiate urine flow from the patient's body at the start of the procedure. The pump can also maintain urine flow during the treatment procedure at a desired flow rate, and can operate continuously, periodically (e.g., at predetermined time intervals), and/or in response to user input and/or detected issues (e.g., unexpected interruptions in urine flow). The pump can also be used to clear air locks and/or other obstructions from the fluid line 119. Additional examples of devices suitable for priming the fluid line 119 with fluid, pumping urine through the fluid line 119, and/or clearing air locks from the fluid line 119 are described with reference to U.S. application Ser. No. 17/659,393, filed Apr. 15, 2022, the entirety of which is incorporated by reference herein.

The urine system 110 can include one or more sensors 114 ("sensor(s) 114") configured to detect the patient's urine output (e.g., an amount and/or rate of urine output). The sensor(s) 114 can be operably coupled to the controller 140 so the controller 140 can monitor and/or compute the patient's urine output based on the data generated by the sensor(s) 114. The urine output can be determined in many different ways, such as based on urine flow (e.g., through the fluid line 119 and/or into the container 112), the amount of urine in the container 112 (e.g., based on the weight of the container 112, level of urine in the container 112, etc.), and/or other properties associated with the urine. The sensor(s) 114 can include one or more of the following: a flow sensor, drip counter, fluid weight sensor, fluid level sensor, float sensor, optical sensor, ultrasonic sensor, and/or other sensors known in the art suitable for measuring a urine output amount and/or rate. In the embodiment of FIG. 1A, the sensor(s) 114 are positioned at the console 105. In other embodiments, however, some or all of the sensor(s) 114 can be at a different location in the system 100, such as on or in the line 119, on or in the container 112, and/or on or in the patient P.

In some embodiments, the sensor(s) 114 can include at least one sensor configured to measure one or more characteristics of the urine, in addition to detecting the patient's urine output. For example, the sensor(s) 114 can be configured to measure urine temperature, urine conductivity, urine oxygenation, urine specific gravity, and/or levels of one or more analytes in the urine (e.g., creatinine, sodium, potassium, etc.). Such characteristics can be useful, e.g., in determining effectiveness of a particular therapy and/or whether the patient P is in or could be approaching a critical condition. For example, urine conductivity and/or urine electrolytes (e.g., sodium) can indicate whether the patient is responding well to the fluid therapy, or whether the patient is in a critical condition and fluid therapy should cease. In some embodiments, urine conductivity (either alone or in combination with urine specific gravity) is used as a proxy for measurements of urine sodium and/or other urine electrolytes, e.g., a higher urine conductivity can correlate to higher urine sodium levels and a lower urine conductivity can correlate to lower urine sodium levels. As another example, urine temperature measurements can be used to detect urine flow (e.g., based on heat loss through the fluid line 119). The urine temperature can also be used as a proxy for the patient's body temperature, which in turn can correlate to the patient's current clinical state.

Optionally, the sensor(s) 114 can include at least one sensor configured to monitor the status of the urine collection procedure, such as whether urine collection is proceeding normally, whether there are interruptions in urine flow, whether there is a blockage or leak in the urine system 110, etc. For example, the sensor(s) 114 can include a leak sensor configured to detect whether a leakage is present in the urine system 110 (e.g., at or near the fluid line 119, catheter 118, and/or container 112). Leaks can be detected based on changes in urine flow rate, changes in pressure, the presence of moisture, or any other suitable parameter. In some embodiments, the controller 140 is configured to analyze the data from the leak sensor and/or other sensor(s) 114 to differentiate between low urine output rates versus leaks in the urine system 110.

As another example, the sensor(s) 114 can include a pressure sensor configured to measure the fluid pressure in the fluid line 119. The controller 140 can use the pressure measurements to monitor the status of urine flow, and optionally, detect whether there are any interruptions (e.g., decreases, sudden stoppages) or other issues with urine collection. In some embodiments, the controller 140 analyzes the pressure measurements to determine whether interruptions are due to low urine flow (e.g., the patient's bladder is empty or nearly empty), an air lock or other obstruction in the fluid line 119, a leak in the urine system 110 and/or a kink in the fluid line 119 and/or catheter 118. The controller 140 can alert the user if manual intervention is helpful or needed (e.g., to clear the obstruction, fix the leak, remove kinks from the fluid line 119, etc.). In embodiments where the urine system 110 includes a pump, the controller 140 can automatically activate the pump and/or increase the pumping rate to clear the obstruction from the fluid line 119.

The hydration system 120 can include at least one hydration fluid source 122 ("fluid source 122"—e.g., a bag, bottle, reservoir, etc.) containing a hydration fluid, such as saline (e.g., a premixed saline solution), Ringler's lactate solution, and/or other any other liquid solution suitable for infusion in the patient P. The hydration fluid can be isotonic, hypertonic, or hypotonic, e.g., depending on the patient's condition and/or other treatment considerations. Optionally, the composition of the hydration fluid (e.g., sodium, chloride, potassium, bicarbonate, etc.) can be varied based on the patient's condition and/or expected or measured electrolyte loss during the treatment procedure.

The fluid source 122 can be connected to the patient P via at least one fluid line (e.g., an IV line or other tubing), such as first fluid line 129*a* and a second fluid line 129*b*. The fluid source 122 can be operably coupled to one or more hydration fluid components 124 for actuating and/or monitoring hydration fluid infusion via the first and second fluid lines 129*a-b*, such as a hydration fluid pump 126 and/or at least one hydration fluid sensor 128 ("fluid sensor 128"). In the illustrated embodiment, the fluid source 122 is fluidly coupled to the hydration fluid pump 126 via the first fluid line 129*a*, and the hydration fluid pump 126 can pump the hydration fluid into the patient P via the second fluid line 129*b*. The hydration fluid pump 126 can be or include a peristaltic pump or other pump suitable for infusing a fluid into the patient's body (e.g., via an IV route or another route).

The fluid sensor 128 can be configured to determine an amount and/or rate of hydration fluid flowing from the fluid source 122 toward the patient P, and can include a flow sensor, pressure sensor, and/or other sensor configured to determine fluid output from the pump 126. Alternatively or in combination, the fluid sensor 128 can monitor hydration infusion rate by measuring the pumping rate of the pump 126 (e.g., the number of rotations of the pump 126 per minute). As described elsewhere herein, the controller 140 can be operatively coupled to the hydration system 120 and can receive sensor data from the fluid sensor 128 to determine a hydration fluid infusion rate. The controller 140 can control the pumping rate of the pump 126 to control the amount and/or rate of hydration fluid provided to the patient P.

Optionally, the amount of hydration fluid in the fluid source 122 can be monitored, e.g., based on weight, volume, fluid levels, flow rates, etc. In such embodiments, the fluid source 122 can be operably coupled to an additional sensor separate from the fluid sensor 128 (not shown), such as a fluid level monitor, float sensor, weight sensor, optical sensor, drip counter, flow measurement sensor, or the like. The additional sensor can provide an independent source of measurement data for determining and/or verifying the amount and/or rate of hydration fluid being provided to the patient P, which can be helpful for improving measurement accuracy.

In some embodiments, the hydration system 120 includes at least one sensor configured to detect the presence of the fluid source 122, such as a location sensor, optical sensor, weight sensor, etc. The hydration system 120 can use the sensor data to automatically determine whether the fluid source 122 is present or absent, e.g., to assess whether the system 100 is ready to initiate the fluid therapy treatment. Optionally, the sensor data can be used to detect if the user is removing the fluid source 122 during the treatment procedure, e.g., to switch an empty or nearly empty fluid source 122 with a new fluid source 122. In such embodiments, the system 100 can automatically pause hydration fluid infusion until the fluid source 122 has been replaced. Accordingly, the user can switch fluid sources 122 without having to inform the system 100 or manually pause the procedure.

The diuretic system 130 can be configured to automatically provide a diuretic to the patient P. The diuretic system 130 can include a diuretic source 134 (e.g., syringe, bag, reservoir, etc.) containing a diuretic, such as bumetanide (Bumex®), ethacrynic acid (Edecrin®), furosemide (Lasix®), torsemide (Demadex®), and/or other diuretics known in the art, each of which may be part of a fluid solution (e.g., a mixture of saline and a diuretic or other agent). In some embodiments, the identity and/or concentration of the diuretic can be received by the controller 140 via user input (e.g., using the display 150), by scanning a barcode of the diuretic source 134 or other container of the diuretic, and/or any other suitable technique.

The diuretic source 134 can be connected to the patient P via a fluid line 139 (e.g., an IV line or other tubing). The diuretic source 134 can also be operably coupled to one or more diuretic components 136 for actuating and/or monitoring diuretic delivery via the fluid line 139. For example, the diuretic components 136 can include a diuretic pump configured to pump the diuretic through the fluid line 139 and toward the patient P. The diuretic pump can include a peristaltic pump, a syringe pump, a metering pump, or other device suitable for delivering the diuretic to the patient P at a plurality of dosage rates. The diuretic pump can deliver the diuretic according to any suitable delivery profile, such as at a controlled continuous rate and/or in controlled boluses delivered at regular intervals through the fluid line 139. Additional details of diuretic delivery profiles are provided below in connection with FIG. 2.

In some embodiments, the diuretic pump is or includes a syringe pump having a mechanical injector or plunger that is operably coupled to the controller 140, such that the controller 140 causes movement of the injector to transfer the diuretic to the patient P. The syringe pump can include or be coupled to an actuator that mechanically drives the injector to control the delivery of the diuretic to the patient P. For example, the actuator can be or include a mechanical actuator, such as a nut for rotating a screw to drive the injector. The syringe pump can also include or be operably coupled to a sensor for detecting the position of the injector. Alternatively or in combination, the diuretic pump can include other types of pumps and/or actuators. For example, the diuretic pump can include a motor, a gearbox operatively connected to the motor, a sensor for measuring rotation of said motor (e.g., a tachometer or an optical encoder), and/or a microcontroller configured to control operation of the motor and monitor the quantity of diuretic delivered to the patient P. As another example, the diuretic pump can include an electric motor, such as a rotary motor, a linear motor, and/or a series of electrically actuated solenoids configured to propel liquid from the diuretic source 134 and through the line 139 toward the patient P.

In some embodiments, the diuretic components 136 include one or more diuretic sensors configured to determine an amount and/or rate of diuretic flowing toward the patient P. The one or more diuretic sensors can include, for example, a flow sensor, weight sensor, and/or other sensor type configured to determine the amount and/or rate of diuretic delivered from the diuretic source 134. Optionally, the diuretic sensors can measure diuretic delivery based on the output from the diuretic pump, such as by monitoring the pumping rate (e.g., number of rotations of the diuretic pump per minute, plunger position, etc.). The diuretic components 136 can include additional functional components, such as an air bubble detector, pressure sensor, extravasation sensor (e.g., ivWatch device), and/or other embedded electronics, e.g., to provide feedback signals to the controller 140 to ensure accurate diuretic infusion and/or monitor infusion status.

The controller 140 is configured to automatically control hydration fluid and/or diuretic infusion (e.g., based at least in part on the patient's urine output) to promote safe and effective diuresis of the patient P. The controller 140 can include one or more processor(s) and tangible, non-transient memory configured to store programmable instructions. The controller 140 can be operably coupled to the urine system 110, hydration system 120 and/or diuretic system 130 to receive data (e.g., sensor data) from and transmit data (e.g., control signals) to the various components of these systems. For example, the controller 140 can receive sensor data from the urine system 110 (e.g., from sensor(s) 114) to determine and/or monitor the patient's urine output. Based on the urine output, the controller 140 can determine an appropriate diuretic dosage amount and/or rate to administer to the patient P, and can cause the diuretic system 130 to deliver the diuretic accordingly. For example, the controller 140 can determine a pumping rate of the diuretic pump to produce the desired delivery profile for the diuretic. Similarly, the controller 140 can determine an appropriate hydration fluid infusion rate for the patient P (e.g., based on the urine output and/or the diuretic dosage rate), and can cause the hydration system 120 to deliver the appropriate hydration fluid amount and/or rate. For example, the controller 140 can determine a pumping rate for the hydration fluid pump 126 to achieve the desired hydration fluid infusion rate. The controller 140 can regulate the diuretic dosage rate and/or hydration fluid infusion rates based on a suitable treatment regimen protocol, e.g., prescribed by a physician and/or managed by the controller 140.

During the procedure, the controller 140 can receive sensor data from the various sensors of the urine system 110, hydration system 120 and/or diuretic system 130 to monitor the urine output, hydration fluid infusion rate, and/or diuretic dosage rate, respectively. The controller 140 can also receive sensor data from additional sensors configured to monitor patient status and/or operational status of the system 100, such as fluid pressure sensors, blood pressure sensors, air bubble detectors, and the like. For example, the controller 140 can be operably coupled to at least one sensor implanted in, attached to, or otherwise associated with the patient P. The sensor(s) can provide data regarding any of the following patient parameters: pressure levels (e.g., pulmonary artery pressure, left atrial pressure), bioelectric measurements (e.g., bioimpedance vector analysis (BIVA)), hemoglobin measurements (e.g., non-invasive hemoglobin measurements), urine oxygenation levels, urine composition (e.g., creatinine, sodium, potassium, chloride, etc.), urine temperature, body temperature (e.g., bladder temperature), oral fluid intake, and the like. The controller 140 can use the data from any of the sensors described herein to monitor treatment progress (e.g., whether the treatment is complete), patient status (e.g., whether the patient is responding well or poorly to treatment), and/or potential safety concerns (e.g., whether the diuresis is too aggressive, whether the patient is exhibiting side effects). The controller 140 can also adjust the hydration fluid infusion rate and/or diuretic dosage rate based on the sensor data. Additionally, the sensor data can also provide feedback to the controller 140 to confirm or verify the effectiveness of the fluid therapy.

The controller 140 can also use other data for monitoring and/or controlling the therapy, such as settings for the system 100, user input, data indicative of a desired treatment regimen (e.g., a programmed diuretic and/or hydration fluid delivery profile over time), and/or other data collected or calculated by the controller 140. In some embodiments, the data used by the controller 140 includes current and/or historical data for the patient P, such as diuretic dosages delivered to the patient P, urine output volume or rate, the amount of hydration fluid infused into the patient P, the weight or change in weight of the patient P at various times during the infusion of the diuretic, indicators of the patient's renal function (e.g., estimated glomerular Filtration Rate (eGFR)), and/or the time(s) during which the patient P was treated with the system 100.

The display 150 (e.g., a touchscreen, monitor, etc.) can include a user interface configured to receive inputs from the user and display outputs to the user. In some embodiments, the display 150 is operatively coupled to the controller 140 and thus can be used to receive user input indicating treatment parameters, such as parameters for urine output, hydration fluid infusion, and/or diuretic dosage. The treatment parameters can include, for example: a desired fluid balance level (e.g., a positive, negative, or neutral fluid balance), target fluid removal volume (e.g., minimum and/or maximum amount of fluid to be removed), desired urine output level (e.g., a total amount of urine output; a target maximum, minimum, and/or average urine output rate), treatment duration (e.g., maximum and/or minimum duration of the treatment procedure; planned duration of the input balance level and/or urine output level), hydration fluid type, hydration fluid infusion rate (e.g., maximum, minimum, and/or average infusion rate), hydration fluid infusion profile (e.g., a function indicating how the amount and/or rate of hydration fluid infusion should vary over time), time limits associated with hydration fluid infusion (e.g., maximum and/or minimum time period for hydration fluid infusion), diuretic type, diuretic dosage (e.g., maximum and/or minimum dosage), diuretic dosage rate (e.g., maximum, minimum, and/or average dosage rate), diuretic dosage profile (e.g., a function indicating how the dosage amount and/or dosage rate of diuretic should vary over time), time limits associated with diuretic delivery (e.g., maximum and/or minimum time period for diuretic delivery), other fluids received by the patient during the procedure (e.g., volume of ingested fluid, volume of fluid from other medical agents besides the diuretic and/or hydration fluid), and/or suitable combinations thereof. Other patient-related inputs may also be received at the display 150 and can include, for example, the patient's sex, weight (e.g., "dry" weight), age, ethnicity, clinical state (e.g., renal function parameters, electrolyte levels such as serum chloride levels), medical history (e.g., outcomes of previous fluid removal procedures), diagnoses (e.g., ADHF, CHF), medications (e.g., whether the patient is diuretic-naïve or diuretic-resistant), dietary factors (e.g., whether the patient is consuming a high-salt or low-salt diet, amount of oral fluid intake), etc.

Alternatively or in combination, the user input via the display 150 can prompt the controller 140 to retrieve treatment parameters (e.g., maximum diuretic dosage, maximum continuous diuretic dosage, and minimum desired urine rate) from tables and/or other data sources. The data sources can be stored in the system 100 (e.g., in a memory associated with the controller 140) and/or can be stored in a separate device (e.g., a remote computing device). In some embodiments, the controller 140 retrieves data from a remote database and/or server via a communication network (e.g., a wired network, a wireless network, a cloud-based network, the Internet, and/or suitable combinations thereof). In such embodiments, the controller 140 can be operably coupled to a communication device and/or interface configured to transmit and receive data via the communication network.

The controller 140 can output the treatment parameters to the user via the display 150 for review and/or feedback. For example, the display 150 can show recommended treatment parameters for the patient P, such as recommendations for the diuretic dosage rate (e.g., initial, maximum, and/or minimum dosage rate), hydration fluid infusion rate (e.g., initial, maximum, and/or minimum infusion rate), urine output rate (e.g., maximum and/or minimum output rate), treatment duration (e.g., maximum time period for diuretic and/or hydration fluid infusion; maximum total treatment duration), and so on. As another example, the display 150 can output one or more predetermined treatment programs so the user can select the appropriate program for the particular patient P. Optionally, the user can modify any of the displayed treatment parameters, if desired.

During the treatment procedure, the controller 140 can output information regarding procedure status to the user via the display 150. For example, the controller 140 can display information regarding any of the following: urine output (e.g., current urine output rate and/or amount, urine output rate and/or amount over time, total amount of urine output so far), hydration fluid infusion (e.g., current infusion rate and/or amount, infusion rate and/or amount over time, total amount of hydration fluid infused so far), diuretic delivery (e.g., current dosage rate and/or amount, dosage rate and/or amount over time, total amount of diuretic delivered so far), fluid balance (e.g., current fluid balance, fluid balance over time, net fluid removal so far), system status (e.g., amount of hydration fluid remaining in the fluid source 122, amount of diuretic remaining in the diuretic source 134, remaining storage capacity in the container 112), treatment time (e.g., treatment start time, projected and/or planned treatment end time, total treatment duration so far), notifications (e.g., alerts, alarms, error messages), and the like. The user can review the displayed information, and, if appropriate, provide input instructing the controller 140 to adjust, pause, and/or stop the treatment procedure.

In some embodiments, the system 100 includes redundancy in the urine system 110, hydration system 120, and/or diuretic system 130 to reduce or minimize treatment interruptions, e.g., due to running out of urine collection capacity, running out of hydration fluid, and/or running out of diuretic. For example, the system 100 can include redundant components (e.g., containers 112, fluid sources 122, and/or diuretic sources 134), which can be stored at predetermined locations (e.g., on or within the console 105 or another portion of the system 100). The controller 140 can be configured to detect the presence of the redundant components, and can automatically or semi-automatically switch between these components so the treatment procedure can continue uninterrupted or substantially uninterrupted. Alternatively or in combination, the system 100 can adjust the timing of user alerts related to urine collection capacity, hydration fluid levels, and/or diuretic levels, based on the availability of redundant components. For example, if redundant components are available, the system 100 can generate alerts at a later time (e.g., closer in time to when the container 112 would be full, when the fluid source 122 would be empty, and/or when the diuretic source 134 would be empty), since the system 100 can automatically switch to using the redundant components, or the user can rapidly perform the switch using the redundant components that are already stored locally at the system 100, rather than having to retrieve replacements from another location.

The lack of interruption in fluid therapy can help ensure effectiveness of the fluid therapy, e.g., by relieving the patient's fluid overload condition as quickly and safely as possible. In some embodiments, even brief interruptions in diuretic delivery and/or hydration fluid infusion can significantly affect the patient's urine output (e.g., cause the urine output rate to drop), which can interfere with therapeutic efficacy and prolong treatment time. The concerns described above regarding diuretic and/or hydration fluid backup supply may be unique to the present technology, e.g., due to the relatively large amounts of diuretic and/or hydration fluid that are utilized over time in some embodiments of the treatment procedures described herein. That is, whereas conventional systems and methods may utilize just a single diuretic source and/or a single hydration fluid source because of the relatively low amount of diuretic and/or hydration fluid administered, the present technology may benefit from multiple diuretic sources and/or hydration fluid sources to ensure treatment continuity. Similarly, the treatment procedures of the present technology can cause the patient P to produce relatively large volumes and/or rates of urine output compared to conventional procedures, such that multiple containers 112 may be helpful to reduce the number of times the user has to empty and/or replace the containers 112 during the procedure.

For example, in some embodiments, the urine system 110 includes two or more redundant containers 112 to ensure fluid therapy does not need to be stopped or interrupted due to the container 112 being full. In such embodiments, the urine system 110 can include a flow control assembly 116 (e.g., valves and/or other flow control components) operably coupled to the controller 140, and configured to selectively direct the urine from the patient P to one or more of the containers 112. The flow control assembly 116 can initially direct the urine received from the patient P to a first container 112. Once the flow control assembly 116 detects or determines the first container is full or nearly full (e.g., based on sensor data from the sensor(s) 114), the flow control assembly 116 can redirect the urine received from the patient P to a second container 112. While urine is being directed to the second container 112, a user can empty the first container 112 or replace the first container 112 with an empty container 112. The flow control assembly 116 and/or controller 140 can generate an alert to the user to indicate the first container is full and needs to be replaced or emptied. This process can be repeated such that fluid management therapy is not inadvertently interrupted due to the containers 112 being full and/or the urine system 110 being unable to accept urine output. In some embodiments, the treatment procedures described herein result in relatively large amounts and/or rates of urine output (e.g., compared to conventional therapies), such that automatic switching between multiple urine containers is advantageous to minimize treatment interruptions. Additional details of the urine system 110 and multiple container 112, and associated devices and methods, are described below with reference to U.S. application Ser. No. 17/659,393, filed Apr. 15, 2022, the entirety of which is incorporated by reference herein.

As another example, the hydration system 120 can include multiple redundant hydration fluid sources 122, e.g., to ensure the hydration fluid infusion can continue without interruption for the entirety of a therapy session and/or to provide an additional time window for switching hydration fluid sources 122 without interrupting hydration fluid infusion. In such embodiments, the hydration system 120 can include a hydration control assembly (e.g., valves and/or other flow control components—not shown) operably coupled to the controller 140, and configured to switch the source of hydration fluid from a first fluid source to a second fluid source. In such embodiments, the hydration control assembly can initially deliver hydration fluid from the first fluid source to the patient P. The hydration control assembly can monitor whether the first fluid source is empty or nearly empty, e.g., based on data from the fluid sensor 128 and/or other sensors associated with the hydration system 120. Once the hydration control assembly detects or determines the first fluid source is empty or nearly empty (e.g., the remaining amount of hydration fluid is below a predetermined threshold), the hydration control assembly can switch to delivering hydration fluid from the second source. The switching process can be repeated such that fluid therapy is not inadvertently interrupted due to the fluid source 122 being empty and/or the hydration system 120 being unable to provide hydration fluid.

The process of switching the hydration fluid source 122 can be performed automatically, semi-automatically, or manually. In some embodiments, semi-automatic or manual switching between the first and second fluid sources may be beneficial to ensure the hydration system 120 does not automatically infuse hydration fluid without user confirmation. In such embodiments, the hydration control assembly and/or controller 140 can output an alert asking the user to verify that the hydration fluid should be switched from the first fluid source to the second fluid source. Upon switching to the second fluid source, the controller 140 can generate an alert to the user to indicate the first fluid source is empty and needs to be replaced. Optionally, the hydration control assembly and/or controller 140 can implement a pre-approval procedure in which the user allows the hydration system 120 to automatically infuse a specified volume of additional hydration fluid. Once that volume has been delivered to the patient P, the user may need to provide re-approval before further automatic infusion of hydration fluid.

In some embodiments, the different fluid sources 122 of the hydration system 120 each provide the same type of hydration fluid. In other embodiments, however, some or all of the fluid sources 122 can provide different types of hydration fluid. The hydration fluids can differ from each other with respect to tonicity, composition, electrolyte content, etc. Depending on the patient's response to diuresis, the hydration system 120 can deliver multiple different hydration fluids to the patient P sequentially or concurrently. For example, if the patient's urine output indicates that the patient P has an electrolyte imbalance (e.g., a positive sodium balance), the hydration system 120 can switch to delivering a hydration fluid that would address the imbalance (e.g., a hydration fluid with lower sodium content). The switching can be performed using any of the techniques and/or devices described above. Accordingly, the particular fluid or fluids delivered to the patient P can be tailored to the patient's particular clinical state and/or response to treatment.

In some embodiments, the diuretic system 130 can include one or more sensors configured to detect whether a backup syringe pump is available for use. In yet another example, the diuretic system 130 can include multiple redundant diuretic sources 134, e.g., to ensure the diuretic delivery can continue without interruption for the entirety of a therapy session and/or to provide an additional time window for switching diuretic sources 134 without interrupting diuretic delivery. For example, if a first diuretic source 134 (e.g., a first syringe or container) is spent, the diuretic can continue to be supplied (e.g., without substantial interruption) via a second diuretic source 134 (e.g., a second syringe or container). The second diuretic source 134 can be connected to the console 105, and can be operably coupled to a sensor configured to detect the presence of the second diuretic source 134 (e.g., a location sensor, optical sensor, weight sensor, etc.). Accordingly, the diuretic system 130 can switch to the second diuretic source 134 if the first diuretic source 134 is empty or nearly empty, and the second diuretic source 134 is present.

In some embodiments, the diuretic system 130 includes two independent diuretic pumps each including its own diuretic source 134. For example, the diuretic system 130 can include syringe pumps each fluidly coupled to its own syringe filled with diuretic. In some cases, such syringes may only be filled by pharmacists or other health care professionals, and thus may not be readily replaced (e.g., in less than a few hours) by the user. When the diuretic system 130 and/or controller 140 detects that the first diuretic source 134 is empty or nearly empty (e.g., below a predetermined threshold), the diuretic supply can be switched (e.g., automatically or manually) to a second diuretic source 134. The switching process can include stopping a first syringe pump fluidly coupled to the first syringe, and starting a second syringe pump fluidly coupled to the second syringe. In other embodiments, the diuretic system 130 includes a single diuretic pump (e.g., syringe pump) connected to two diuretic sources 134. In such embodiments, case switching between the first and second diuretic sources 134 can involve using a diuretic control assembly (e.g., valves and/or other flow control components) to switch the diuretic pump from delivering diuretic from the first diuretic source 134 to the second diuretic source 134. The switching process can be repeated such that fluid therapy is not inadvertently interrupted due to the diuretic source 134 being empty and/or the diuretic system 130 being unable to provide diuretic.

The process of switching the diuretic source 134 can be performed automatically, semi-automatically, or manually. In some embodiments, manual or semi-automatic switching between the first and second diuretic sources 134 may be beneficial to ensure the diuretic system 130 does not automatically infuse a large volume of diuretic without user confirmation. In such embodiments, the controller 140 can output an alert asking the user to verify that the diuretic should be switched from the first diuretic source 134 to the second diuretic source 134. Upon switching to the second diuretic source 134, the controller 140 can generate an alert to the user to indicate the first diuretic source 134 is empty and needs to be replaced. Optionally, the controller 140 can predict a time point and/or time range when the first diuretic source 134 will be empty (e.g., based on the diuretic dosage rate), and can output a notification so the user can order or otherwise prepare a replacement diuretic source 134 before the first diuretic source 134 runs out. Moreover, the diuretic control assembly and/or controller 140 can implement a pre-approval procedure in which the user allows the diuretic system 130 to automatically delivery a specified additional dosage of diuretic. Once that dosage has been delivered to the patient P, the user may need to provide re-approval before further automatic delivery of diuretic.

In some embodiments, the different diuretic sources 134 of the diuretic system 130 each provide the same type of diuretic. In other embodiments, however, some or all of the diuretic sources 134 can provide different types of diuretics. Depending on the patient's response to diuresis, the diuretic system 130 can deliver multiple different diuretics to the patient P sequentially or concurrently. For example, the diuretic system 130 can initially deliver a first diuretic to the patient P from a first diuretic source 134. If the patient P responds poorly to the first diuretic (e.g., the urine output rate does not increase or increases very slowly), the diuretic system 130 can switch to delivering a second, different diuretic from a second diuretic source 134. The diuretic system 130 can continue delivering the first diuretic concurrently with the second diuretic, or can terminate delivery of the first diuretic when the second diuretic is delivered. The switching can be performed using any of the techniques and/or devices described above. As another example, if the patient P does not respond well to a single diuretic, the diuretic system 130 can simultaneously administer multiple diuretics to the patient P. The ratio of the different diuretics can be varied as appropriate to elicit a suitable urine output rate. In other embodiments, however, rather than automatically administering additional diuretics, the diuretic system 130 can output a notification recommending that the user manually administer a different diuretic to the patient P and/or requesting that the user approve administration of a different diuretic, which may be beneficial for patient safety.

The system 100 illustrated in FIG. 1A can be configured in many different ways. For example, the locations of the various components of the system 100 can be altered, e.g., the urine system 110, hydration system 120, and/or diuretic system 130 can be at different locations in the console 105. As another example, any one of the urine system 110, hydration system 120, or diuretic system 130 can be part of a separate system or device (e.g., a separate console), or can be omitted altogether. For instance, in some embodiments, the urine system 110 is replaced with a mechanism for monitoring the patient's urine output that does not require the catheter 118 and/or urine collection, such as an ultrasound sensor that measures the patient's bladder volume. The ultrasound sensor can be implemented as a patch or similar device that is coupled to the patient's body. The controller 140 can process the ultrasound sensor data to detect changes in the bladder volume, and can determine the corresponding amount and/or rate of urine output based on the bladder volume. The use of non-invasive urine monitoring mechanisms such as an ultrasound sensor can allow the treatment procedures described herein to be performed in outpatient and/or home settings, and would allow the urine bag to be emptied without disturbing the continuous and/or discontinuous (e.g., every minute, two minutes, etc.) measurement of urine flow or volume.

As another example, in some embodiments, the hydration system 120 is omitted such that diuresis is performed without hydration fluid infusion, or the hydration fluid is infused manually. Diuresis with hydration fluid infusion may be more beneficial for patients with low serum chloride levels (e.g., patients with low-salt diets), while patient with high serum chloride levels (e.g., patients with high-salt diets) may tolerate diuresis with little or no hydration fluid infusion. Optionally, the hydration fluid infusion rate can be varied at least partially based on the patient's serum chloride levels, e.g., lower amounts and/or rates of hydration fluid infusion can be used if the patient's serum chloride level is high (e.g., greater than or equal to 105 mmol/L).

In yet another example, the diuretic system 130 can be omitted such that no diuresis is performed, or the diuresis is performed manually. In such embodiments, the system 100 can provide automated fluid replacement via the hydration system 120 and/or can automatically monitor the patient's urine output via the urine system 110, but the diuretic would be administered manually by a healthcare professional in accordance with techniques known to those of skill in the art.

Figure 1B:
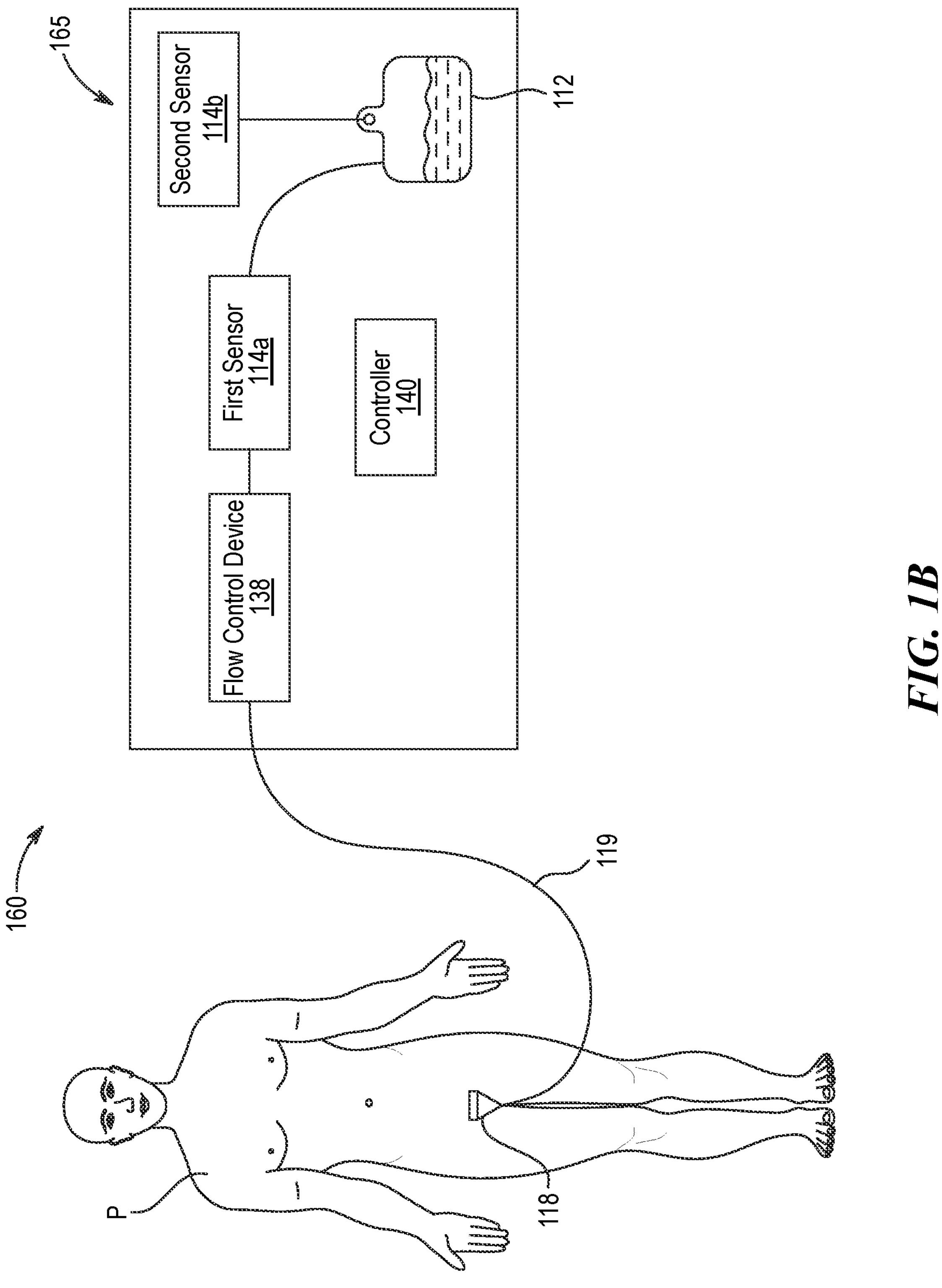

FIG. 1B is a partially schematic view of another fluid management system 160 ("system 160") for monitoring urine output and/or controlling fluid infusion into a patient P, in accordance with embodiments of the present technology. As shown in FIG. 1B, the system 160 can include a console 165 (e.g., the console 105; FIG. 1A) and many of the same features of the system 100, including the container 112 having a drain valve 113, the catheter 118, the fluid line 119, and the controller 140 (as previously described with reference to FIG. 1A). The system 160 can further include a flow control device 138 (e.g., a pinch valve), and multiple sensors for monitoring urine production and some of the sensors can be redundant sensors. The flow control device 138 can be operably coupled to the controller 140 and be configured to regulate flow from the patient to the container 112. In some embodiments, the flow control device 138 includes a pinch valve that regulates flow by externally pinching the fluid line 119. As shown in FIG. 1B, the flow control device 138 is upstream of a first sensor 114*a*. However, in other embodiments the flow control device 138 can be downstream of the first sensor 114*a*.

The sensors 114 can include (i) a first sensor 114*a* (e.g., a flow sensor, thermal flow sensor (e.g., the Sensirion SLF3x Liquid Flow Sensor), a mechanical paddlewheel type flow sensor, an ultrasonic flow sensor, etc.) coupled (e.g., fluidly coupled) to the fluid line 119 and the catheter 118 and configured to measure a flow rate of urine from the patient P, and (ii) a second sensor 114*b* (e.g., a weight sensor) coupled to the container 112 and configured to measure weight of the container 112. The first and second sensors 114*a-b* can be operably coupled to the controller 140. For embodiments in which the first sensor 114*a* comprises an ultrasonic flow sensor, the ultrasonic flow sensor can be positioned external to the fluid line 119 and thus not contact the fluid therein.

As disclosed elsewhere herein, the signal associated with urine production from the patient can be used by the system, e.g., to determine how much diuretic and/or hydration fluid to administer (e.g., automatically controlled administration of a diuretic and/or a hydration fluid). Accordingly, obtaining an accurate and reliable urine output signal can be beneficial. In such embodiments, the signal from the first or second sensor 114*a-b* can be compared to the signal from the other one of the first or second sensor 114*a-b* to ensure accuracy of measurement. The signals can be obtained at regular intervals (e.g., every second, 30 seconds, minute, 2 minutes, 5 minutes, 10 minutes, etc.), and can be used to produce average flow rates on a rolling basis or to calculate total urine volume over a given time period. For example, based on the signals obtained from the first and second sensors 114*a-b*, an average flow rate or patient urine output rate can be determined and continuously updated, e.g., for the previous minute.

In some embodiments, the signal from the second sensor 114*b* can be used as the primary source or input and the signal from the first sensor 114*a* can be used as a backup or secondary signal source. Alternatively, the signal from the first sensor 114*a* can be used as the primary source and the signal from the second sensor 114*b* can be used as a secondary signal source. The primary source may switch between the first and second sensors 114*a-b* if (e.g., only if) the current sensor serving as the primary source fails, is not available (e.g., taken offline), or other predetermined condition is met. For example, in some embodiments the signal from the second sensor 114*b* can be used as the primary source unless and/or until (i) the weight of the container 112 is above a predetermined threshold, indicating the container 112 is nearly full and needs to be drained, (ii) the weight of the container 112 is decreasing, likely indicating the container 112 is being drained and thus rendering the second sensor 114*b* less able to produce an accurate urine flow measurement, (iii) the weight of the container 112 is increasing at a rate less than expected, or is decreasing in weight, indicating the container 112 is being drained and thus rendering the second sensor 114 less able to produce an accurate urine flow measurement, and/or (iv) there is a discrepancy between the signals of the first and second sensors 114*a-b*, indicating the container 112 is being drained and/or one of the signals is not accurate. If one or more of these conditions is met, the system 160 or controller 140 can (i) be configured to preference one of the sensors over the other, and/or (ii) analyze the signals from both sensors and select the most reliable signal based on other operating conditions (e.g., the immediately previous obtained urine output rate, the average urine output rate, the diuretic dosage, the hydration infusion, etc.).

In such embodiment where a sensor used as the primary source is deactivated, that sensor may not be reactivated until another condition is met. For example, if the signal from the second sensor 114*b* is removed from being the primary source, e.g., due to a decrease in weight of the container 112, the signal from the second sensor 114*b* may not reengage as the primary source until a predetermined condition (e.g., an increase in weight of the container 112) occurs or a time (e.g., 30 seconds, 1 minute, 2 minutes, etc.) after the predetermined condition has elapsed. If the predetermined condition (e.g. an increase in weight of the container) is not met after a pre-specified time period, an alert may be generated to indicate to the user that an unexpected condition has been encountered, such as a suggestion that the drain valve 113 has not been closed, or that the urine bag is leaking.

In some embodiments, a determined discrepancy between the first and second sensors 114*a-b* can identify a potential fault in the system (e.g., faulty sensor) and cause the system 160 to stop all or portions of the fluid therapy, and/or alert the user that such discrepancy exists. In some embodiments, depending on which of and/or how long the first or second sensors 114*a-b* are offline or determined to be inaccurate, the system 160 or controller 140 may alter other aspects of therapy provided to the patient. For example, the amount of diuretic and/or hydration fluid provided to the patient may be maintained or decreased. In some embodiments, the first and second sensor can be tested during preparation of the system 160 for connection to the patient, such that if a failure of either of the sensors 114*a-b* is detected, or if there is a large discrepancy between the readings of the sensors 114*a-b*, an alert can be generated prior to the initiation of therapy, preventing the use of the system in a non-functional state.

In some embodiments, the first sensor 114*a* (i.e., the flow sensor) is omitted and the second sensor 114*b* (i.e., the weight sensor) is relied on to provide a urine flow output from the patient. In such embodiments, the sensor data obtained from the second sensor 114*b* is utilized to determine an average urine flow rate over a period of time, e.g., based on the rate of change of weight of the container 112. Additionally, in such embodiments, when the system 160 determines via the second sensor 114*b* that the weight of the container 112 is decreasing or not increasing at an expected rate, which may indicate the container 112 is being drained, the system can ignore the signal from the second sensor 114*b* for a predetermined period of time (e.g., 1 minute, 2 minutes, 5 minutes, etc.), before again relying on the signal to provide the urine flow output. During this predetermined period of time, the diuretic and/or hydration fluid provided to the patient can be maintained and/or decreased.

Advantageously, the system 160 and other embodiments of the present technology can remain operational and provide therapy even when the container 112 is replaced and/or emptied. For example, because the first sensor 114*a* is upstream of the container 112 and can be a flow sensor not dependent on weight of the container, the urine output of the patient can be monitored while the container is being replaced and/or emptied. As such, unlike other embodiments only having a sensor configured to measure weight of the container 112, and thus unable to provide accurate urine output measurements when the container is being replaced and/or emptied, embodiments of the present technology enable the system 160 to continue providing therapy uninterrupted. Additionally or alternatively, embodiments of the present technology enable a healthcare professional to drain the container 112 (e.g., via a drain valve 113 of the container 112) without (i) having to replace the container 112 and remove the container 112 from the system, and (ii) using the interface of the system, which may be prohibited and/or can inadvertently lead to interrupting fluid therapy of the patient.

The system 100 can optionally include or be used in combination with additional systems or devices, such as systems or devices configured to perform any the following functions: administering other medications and/or agents besides the diuretic and hydration fluid (e.g., heart failure medication), monitoring other patient parameters besides urine output (e.g., blood pressure, weight, heart rate, blood oxygenation, respiratory rate, temperature), and/or performing other types of medical procedures on the patient P concurrently or sequentially with the fluid removal procedure (e.g., dialysis, ultrafiltration).

Figure 2:
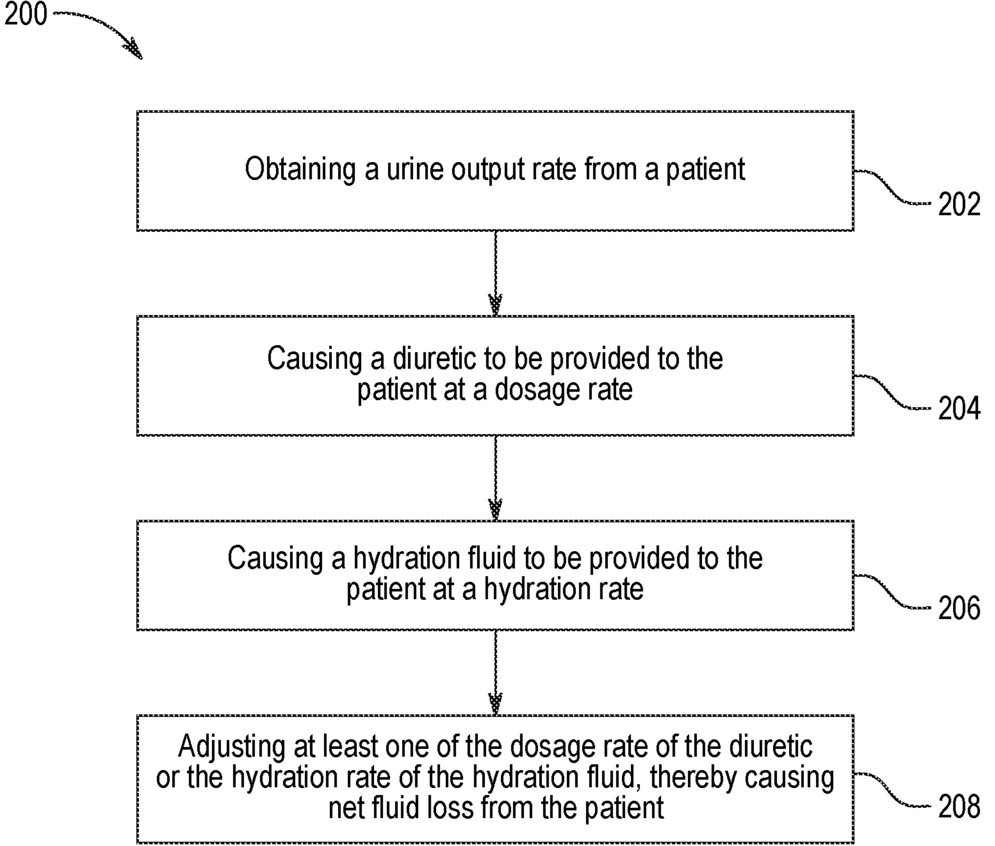
FIG. 2 is a flow diagram of a method for treating a patient, in accordance with embodiments of the present technology.

FIG. 2 is a flow diagram of a method 200 for treating a patient, in accordance with embodiments of the present technology. In some embodiments, the method 200 is used to treat the patient for fluid overload by removing fluid from the patient to produce a negative fluid balance (net fluid loss). The method 200 (and the other methods described herein) include one or more steps, blocks, phases, acts, portions, process portion, operations, or the like. The method 200 can be performed by any embodiment of the systems and devices described herein, such as the system 100 of FIG. 1A and/or the system 160 of FIG. 1B. In some embodiments, some or all of the steps of the method 200 are performed by a system or device including one or more processors and a memory storing instructions that, when executed by the one or more processors, cause the system or device to perform one or more of the steps described herein. For example, the method 200 can be performed by the controller 140 of the system 100 of FIG. 1A or the system 160 of FIG. 1B. Optionally, some or all of the steps of the method 200 can performed automatically or semi-automatically, with little or no human intervention.

The method 200 can include obtaining a urine output rate from a patient (process portion 202). The urine output rate can be obtained from a urine monitoring and/or collection system connected to the patient, such as the urine system 110 of FIG. 1A. The system can determine the urine output rate based on received input data, such as data from one or more sensors (e.g., the sensor(s) 114 of FIGS. 1A and/or 1B). As described above, the sensor(s) can be configured to measure the urine output rate based on flow rate, weight (e.g., of the container 112 of FIGS. 1A and 1B), volume, fluid level, and/or any other suitable parameter. The urine output rate can be calculated based on the received input, e.g., by a controller (e.g., controller 140 of FIGS. 1A and/or 1B) operatively coupled to the sensor(s). The urine output rate can be a current rate or an average rate measured over a predetermined time period (e.g., the previous 5 or 10 minutes). The urine output rate can be updated on a continuous or recurring basis (e.g., every 30 seconds, 1 minutes, 2 minutes, etc.). In some embodiments, the urine output rate is obtained concurrently with some or all of the other process portions 204, 206, 208 of the method 200 to provide continuous or substantially continuous urine output monitoring through the entirety of the method 200.

The method 200 can include causing a diuretic to be provided to the patient at a dosage rate (process portion 204). The diuretic can be or include furosemide, bumetanide, ethacrynic acid, torsemide, combinations thereof, and/or other diuretics known in the art. In some embodiment, the diuretic is delivered as part of a solution including saline or other hydration fluid(s) mixed therewith. The diuretic can be provided automatically or semi-automatically by a diuretic system connected to the patient, such as the diuretic system 130 of FIG. 1A. The diuretic system can be operably coupled to a controller (e.g., controller 140 of FIGS. 1A and/or 1B) for causing diuretic delivery in accordance with a planned and/or pre-programmed treatment procedure.

In some embodiments, the treatment procedure includes multiple phases, and each phase is associated with a different delivery profile for the diuretic. In such embodiments, process portion 204 can be performed as part of an initial phase to determine an appropriate diuretic dosage rate for treating the patient (also known as a "dosage determining phase"). In the dosage determining phase, the diuretic is injected at an initial dosage rate, and the dosage rate can then be gradually increased to elicit an increase in the patient's urine output rate. The diuretic dosage rate can be increased according to a desired function or delivery profile, such as a continuous function, a step-wise function, or a combination thereof). The function can include iteratively increasing the dosage rate linearly, exponentially, according to a polynomial function, and/or any other suitable ramp function or profile. In some embodiments, the diuretic is delivered in a manner such that a subsequent dosage rate is a predetermined percentage (e.g., at least 5%, 10%, 15%, 25%, etc.) above the immediately previous dosage rate. The predetermined percentage can increase or decrease over time, e.g., depending on the desired fluid therapy and/or patient considerations. Optionally, the diuretic can be provided in a manner that doubles the diuretic dosage rate or total diuretic within a period of time (e.g., 10 minutes, 15 minutes, 20 minutes, or within a range of 10-20 minutes). In other embodiments, however, the dosage determining phase can include one or more time periods during which the diuretic dosage rate does not increase and/or is held substantially constant. The dosage determining phase can continue until the patient's urine output reaches or exceeds a desired threshold rate and/or a predetermined time period has elapsed, at which point the diuretic dosage rate can be adjusted, as described with reference to process portion 208 below.

The method 200 can include causing a hydration fluid to be provided to the patient at a hydration rate (process portion 206). The hydration fluid can comprise saline and/or other fluids having sodium, and can be provided automatically or semi-automatically by a hydration fluid system connected to the patient, such as the hydration system 120 of FIG. 1A. The hydration fluid can be provided before, during, and/or after providing the diuretic in process portion 204 (e.g., before, during, and/or after the dosage determining phase). Intravenous infusion of hydration fluid containing electrolytes (e.g., sodium and/or chloride) can increase diuretic efficiency, which is counterintuitive since a goal of fluid therapy is net removal of fluid. Hydration fluid can also reduce or inhibit intravascular depletion, decreases in cardiac output, and/or decreases in renal perfusion, among other benefits.

In some embodiments, the hydration fluid is provided to the patient based at least in part on the corresponding urine output rate, e.g., to drive net fluid loss from the patient. For example, the hydration rate can be less than the urine output rate. In some embodiments, the hydration rate is a percentage of the urine output rate (e.g., 90%, 80%, 70%, 60%, 50%, 40%, 30%, 20%, or 10% of the urine output rate) for a given range of urine output rates (e.g., from 0 ml/hr to 1000 ml/hr). Optionally, the percentage can be higher for certain parts of the range (e.g., for the lower end of the range to reduce the likelihood of hypotension) and/or lower for other parts of the range (e.g., for the higher end of the range to increase net fluid loss). As another example, the hydration rate can substantially match the urine output rate (e.g., 100% of the urine output rate) for an initial amount of urine output by the patient (e.g., at least the initial 150 ml, 200 ml, or 250 ml), for an initial time period (e.g., the first hour, 2 hours, or 3 hours), and/or until the patient's urine output rate reaches a predetermined threshold. Subsequently, the hydration rate can be adjusted to be less than the urine output rate. In a further example, the hydration rate may be determined based on whether the urine output rate is above or below one or more different thresholds, with the difference between the urine output rate and hydration fluid rate increasing as the urine output rate increases. In such embodiments, the difference between the urine output rate and the hydration fluid rate can increase (with the urine rate being higher than the hydration fluid rate) as the urine output rate increases, and thus the net fluid loss from the patient can increase as the urine output rate increases.

The method 200 can include adjusting at least one of the dosage rate of the diuretic or the hydration rate of the hydration fluid, thereby causing net fluid loss from the patient (process portion 208). For example, the (i) diuretic dosage rate can be adjusted, (ii) the hydration rate can be adjusted, or (iii) the diuretic dosage rate and the hydration rate can both be adjusted. In some embodiments, the diuretic dosage rate is adjusted after the dosage determining phase of the treatment procedure is complete. As discussed above regarding process portion 204, the dosage determining phase can end when (i) a predetermined amount of time has elapsed since the initial diuretic administration, and/or (ii) the urine output rate is or becomes greater than or equal to a predetermined threshold rate. The treatment procedure can then switch to a phase in which the diuretic dosage rate is adjusted to a dosage rate configured to maintain the patient's urine output rate at or above a desired output rate to cause net fluid loss (also known as a "continuous delivery phase" or "fluid reduction phase").

The adjusted diuretic dosage rate can be the initial dosage rate for the fluid reduction phase, and can be determined in many different ways. For example, the adjusted diuretic dosage rate can be based on the outcome of the dosage determining phase. The adjusted diuretic dosage rate can be less than or equal to the diuretic dosage rate at the end of the dosage determining phase (e.g., the dosage rate when the patient's urine output reaches or exceeds the target threshold). Decreasing the diuretic dosage rate can decrease the rate of increase in urine output rate (e.g., cause the patient's urine output to approach a constant or substantially constant rate) but without actually decreasing the urine output rate itself. Additionally or alternatively, the decrease in diuretic dosage rate can maintained the patient's urine output rate at a predetermined rate and/or within a predetermined range (e.g., no more than 5%, 10%, or 20% variability from a predetermined rate).

In some embodiments, the adjusted diuretic dosage rate is a predetermined percentage or fraction of the current dosage rate (e.g., the dosage rate at the end of the dosage determining phase) or a predetermined percentage of the cumulative diuretic dosage amount (e.g., the cumulative amount delivered during the dosage determining phase). For example, the adjusted dosage rate can be a predetermined percentage (e.g., 10%, 15%, 20%, 25%, 30%, or within a range of 10-30%) of a value of the total amount of diuretic delivered to the patient at that time. For example, if the total amount delivered is 100 mg, and the predetermined percentage is 25%, then the adjusted dosage rate can be 25 mg/hr. In some embodiments, the percentage used to calculate the adjusted diuretic dosage rate is based on a pharmacokinetic characteristic of the particular diuretic being infused. For example, the percentage can be 20% for furosemide, such that if 50 mg of furosemide is infused in 60 minutes, then the adjusted diuretic dosage rate can be 10 mg/hr.

In some embodiments, process portion 208 includes delivering the diuretic at the adjusted diuretic dosage rate until the fluid reduction phase is complete, e.g., until a predetermined period of time has elapsed and/or until an estimated amount of excess fluid is removed from the patient, and/or until the patient's urine rate drops below a predetermined threshold and the total fluid removed from the patient exceeds the estimated amount of excess fluid. During the fluid reduction phase, the diuretic dosage rate can be constant or substantially constant (e.g., no more than 5%, 10%, or 20% variability from the initially determined adjusted diuretic dosage rate). In other embodiments, however, process portion 208 can include making additional adjustments to the diuretic dosage rate during the treatment procedure (e.g., increasing and/or decreasing the diuretic dosage rate). The adjustments can be based on whether one or more of a predetermined set of conditions is met, such as whether the urine output rate is too high and/or increasing. The set of conditions can include (i) an average urine rate being greater than a predetermined rate for a period of time, (ii) an average rate of change of the urine rate being greater than a predetermined rate of change, and/or (iii) a diuretic dosage rate being greater than a predetermined dosage rate. If some (e.g., two) or all of the conditions are met, the diuretic dosage rate can be decreased (e.g., by a predetermined amount or percentage), also referred to herein as "down-titration."

In some embodiments, a down-titration is performed only if all or a majority of the above conditions are met, which can avoid unnecessarily decreasing the diuretic dosage rate, thereby allowing urine output rates to remain high and avoiding unnecessary interruptions to the treatment procedure. For example, whereas other methodologies may interrupt fluid therapy and decrease the diuretic dosage rate (e.g., to zero mg/hr) when the urine rate is just too high, the process described herein can only decrease the dosage rate (e.g., to a non-zero or zero dosage rate) when the urine output rate is both high and continuing to increase. Stated differently, the process herein can prevent the diuretic dosage rate from being unnecessarily decreased when urine rates are temporarily high (e.g., above the predetermined rate), but are trending downward. This approach can prevent or inhibit over-diuresis, excess fluid loss and/or electrolyte loss, as well limit unnecessary exposure of the patient to additional diuretic. Additionally, because the diuretic dosage rate can be down-titrated, rather than stopping the diuretic entirely, the fluid therapy can continue (albeit at lower urine output rates) without needing to completely restart the procedure.

As another example, the additional adjustments to the diuretic dosage rate in process portion 208 can include increasing the diuretic dosage rate, also referred to herein as "re-ramping" or "up-titration." In some embodiments, re-ramping is performed if urine output rates are too low and/or decreasing, as determined based on a set of conditions. The set of conditions can include (i) the average urine rate being below a predetermined threshold rate for a predetermined period of time, and/or (ii) more than a predetermined amount of debt has accumulated over the predetermined period of time. "Debt" can be defined as the area on a plot between the urine output rate and a set rate (e.g., 325 ml/hr), and can represent how much of and for how long the urine output rate has been below the set rate. If some or all of the conditions are met, re-ramping can be performed by incrementally increasing the diuretic dosage rate until (i) a predetermined amount of time has elapsed, and/or (ii) the urine output rate is or becomes greater than or equal to a predetermined threshold rate. The re-ramp process can be identical or generally similar to the dosage determining process previously described with reference to process portion 204.

The re-ramping process can be performed automatically, semi-automatically, or manually. In some embodiments, re-ramping is a semi-automatic or manual process requiring user approval, e.g., for regulatory and/or safety reasons. In such embodiments, the system can output a notification to the user (e.g., via the display 150 of FIG. 1A) instructing the user to confirm that re-ramping should be initiated. Optionally, the system can implement a pre-approval procedure in which the user can allow the system to automatically perform re-ramping under certain conditions (e.g., within a specific time period, until a certain urine output volume and/or rate is achieved, for a maximum diuretic amount and/or dosage rate, etc.). This approach can allow for automatic re-ramping under limited circumstances, which can reduce the amount of human intervention during the treatment procedure and improve the responsiveness of the system to the patient's current state. Once the pre-approval conditions have elapsed, the user may need to provide re-approval before additional automatic re-ramping is allowed.

In some embodiments, process portion 208 also includes adjusting the diuretic dosage rate in response to a detected blockage (e.g., an air lock, a kink in a fluid line, etc.) in the urine collection system. For example, an air lock can be any partial or complete obstruction of fluid flow due to trapped gas (e.g., air) within a fluid system. Examples of situations where air locks may arise are described in U.S. patent application Ser. No. 17/659,393, filed Apr. 15, 2022, the entirety of which is hereby incorporated by reference. As described elsewhere herein, air locks may produce an artificial drop in urine output rates, which can affect the determination of the diuretic dosage rate (e.g., result in a diuretic dosage rate that is too high). In some embodiments, the presence of an air lock is detected based on a period of little or no urine output (due to the air lock blocking urine flow), followed by a sudden large bolus of urine output (due to built-up pressure in the fluid line clearing the air lock). When the system detects that an air lock or other blockage was or is present, the system can compensate by adjusting the diuretic dosage rate to the dosage rate that should have been used if the air lock or other blockage had not occurred. The appropriate dosage rate can be determined based on historical data (e.g., the diuretic dosage rate before the air lock occurred, a diuretic dosage rate calculated from the patient's urine output rate before the air lock occurred, urine volume measured when the airlock clears, etc.).

Alternatively or in combination, process portion 208 can include adjusting the hydration rate, e.g., by increasing or decreasing the hydration rate based on the patient's urine output rate to drive net fluid loss from the patient. For example, as previously described, the hydration rate can initially match the patient's urine output rate for a set of initial conditions (e.g., certain time period, initial urine output amount, and/or initial urine output rate). Once the initial conditions have elapsed, the hydration rate can be maintained at a rate lower than the urine output rate (e.g., a percentage of the urine output rate) so the patient exhibits net fluid loss during the fluid reduction phase. The hydration rate can be determined in various ways, such as a percentage or fraction of the patient's urine output rate, based on whether the urine output rate is above or below a number of different thresholds (e.g., with the difference between the urine output rate and hydration rate increasing as the urine output rate increases), and/or any other suitable approach.

Optionally, the diuretic dosage rate and/or hydration rate can be adjusted based on factors other than patient's urine output rate. For example, the diuretic dosage rate and/or hydration rate can be adjusted based on the patient's blood pressure in order to avoid placing the patient in a hypotensive state. In some embodiments, if the patient's blood pressure level is too low (e.g., below a threshold value or range), the system can avoid increasing the diuretic dosage rate and/or can decrease the diuretic dosage rate for a certain period of time. Alternatively or in combination, the system can increase the hydration rate (e.g., to the maximum allowable hydration rate and/or to provide a desired fluid replacement profile (e.g., a 100% match to the patient's urine output rate)) for a certain period of time if low blood pressure levels are detected. The system can also output an alert indicating that the patient's blood pressure level is low so a user can check on the patient's status. Optionally, the system can take both blood pressure levels and urine output rates into account, e.g., the system can generate alerts and/or can adjust the diuretic dosage rate and/or hydration rate if the patient's blood pressure is low and the patient's urine output rate drops. This approach can improve patient safety and control over the treatment procedure.

In some embodiments, some or all of the process portions of the method 200 are performed as part of a medical procedure for treating the patient for a fluid overload condition. The method 200 can be used as a primary, standalone therapy for treating fluid overload, or can be used in combination with other therapies (e.g., as a post-primary therapy to reduce the likelihood of rehospitalization). The method 200 can be performed in any suitable setting, such as an inpatient setting or an outpatient setting. In embodiments where the method 200 is performed as an outpatient therapy, the overall duration of the method 200 can be reduced (e.g., to no more than 10 hours, 5 hours, 4 hours, 3 hours, 2 hours, or 1 hour).

The method 200 illustrated in FIG. 2 can be modified in many different ways. For example, any of the process portions of the method 200 can be omitted, such as process portion 204 or 206. In some embodiments, process portion 204 is omitted so that the method 200 controls hydration fluid infusion but not diuretic delivery, or so that the method 200 does not involve any diuretic delivery at all. Similarly, process portion 206 can be omitted so that the method 200 controls diuretic delivery but not hydration fluid infusion, or so that the method 200 does not involve any hydration fluid infusion at all. As another example, some or all of the process portions of the method 200 can be performed in a different order and/or repeated (e.g., any of process portions 202, 204, 206, and/or 208). In a further example, the method 200 can optionally include additional process portion not shown in FIG. 2 (e.g., causing delivery of additional medications, obtaining parameters other than urine output rate, etc.).

The present technology can provide many advantages for treating fluid overload and/or managing patient fluid levels. For example, embodiments of the present technology have been shown to consistently reduce the fluid volume in patients faster and safer than conventional treatment systems and methods. For example, whereas conventional methods can typically take at least five days to remove 4-5 L of net fluid volume, embodiments of the present technology have been shown to remove 4-5 L liters of net fluid volume in no more than 24 hours. Additionally, embodiments of the present technology have also been shown to remove significant amounts of salt via high sodium urine from patients. This can reduce the likelihood of the patient reaccumulating fluid after discharge, which can lead to reductions in rehospitalization rates. Moreover, embodiments of the present technology can automatically and continuously monitor urine output, hydration fluid infusion, and/or diuretic delivery to mitigate patient safety concerns (e.g., over-diuresis and/or hypotension) during the treatment procedure.

Embodiments of the present technology can provide various benefits, such as any of the following: (i) optimizing net fluid volume removal; (ii) reducing the time needed to achieve desired net fluid removal by allowing physicians to use higher diuretic dosages and/or dosage rates earlier in treatment compared to conventional treatments; (iii) avoiding or reducing risk of adverse events such as over-diuresis, dehydration, and/or intravascular depletion; (iv) quickly assessing if a patient is diuretic resistant; and (v) providing a record of treatment data. Embodiments of the present technology may obtain an average net fluid removal rate (e.g., average urine output rate minus average hydration fluid infusion rate) of at least 225 ml/hr, which provides 3.4 L per day of net fluid volume removal based on introducing 2 L of fluid per day orally or through IV infusion. This rate of fluid removal, while replacing sodium, may reduce the overall length of stay and/or provide enhanced decongestion.

Figure 3A:
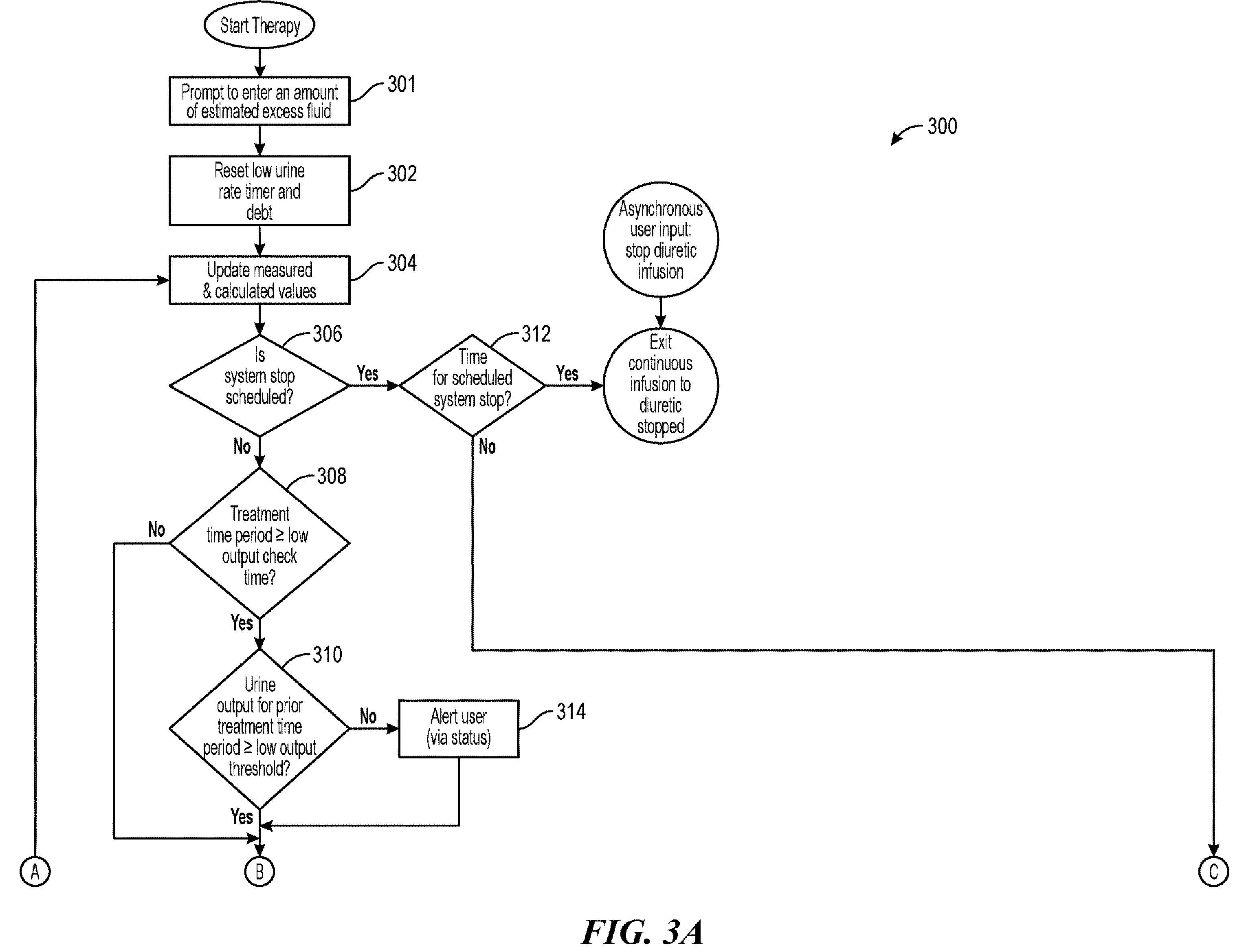
FIGS. 3A-3C are flowcharts for managing a patient's urine output based at least in part on a target fluid loss of the patient, in accordance with embodiments of the present technology.
Figure 3B:
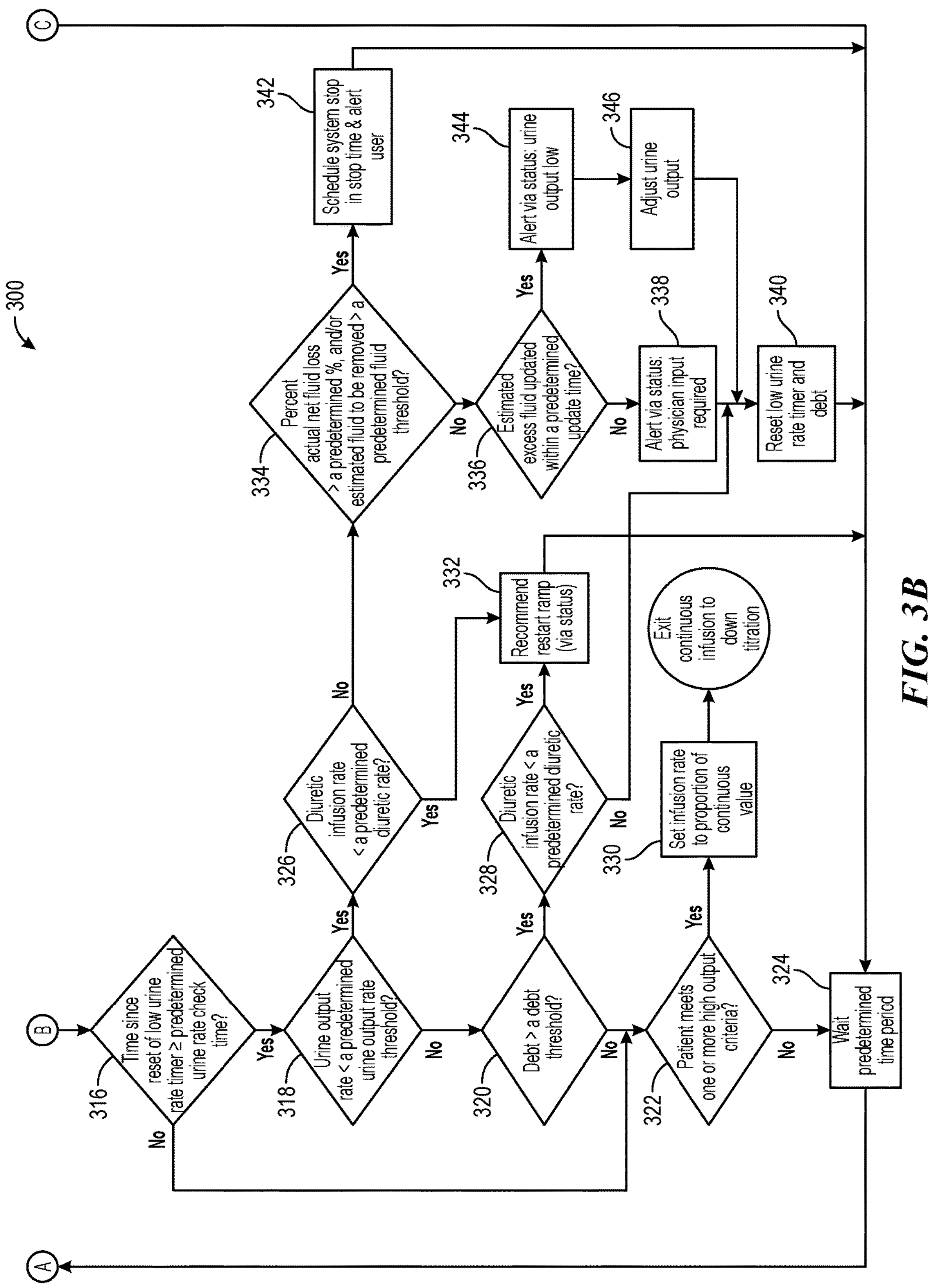
Figure 3C:
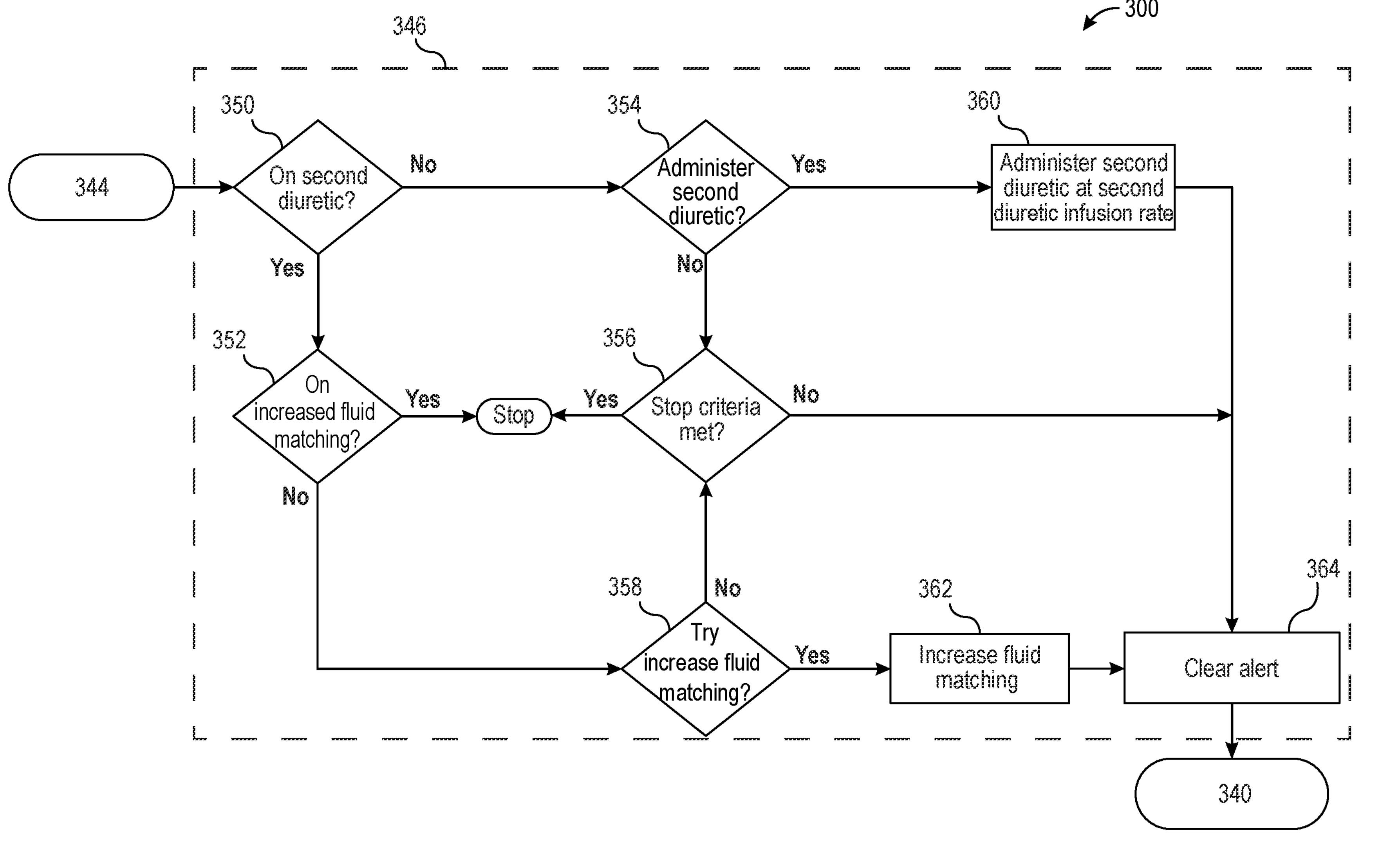

II. Fluid Therapy Based on Estimated Excess Fluid, and Associated Systems and Methods FIGS. 3A-3C are flowcharts of a system 300 for managing a patient's urine output based at least in part on a desired and/or estimated amount of excess fluid to be removed from the patient. The features of the embodiments described in FIGS. 3A-3C are suitable for use with the system 100 of FIG. 1A, the system 160 of FIG. 1B, and/or the method 200 of FIG. 2. Any of the features of the embodiments of FIGS. 3A-3C can be combined with each other and/or incorporated into any of the other embodiments of the present technology. Additionally, any actions or process portions described as being performed by the system 300 can be performed automatically by the system 300 and/or in response to one or more inputs from a user, e.g., based at least partially on an output of the system 300.

As described elsewhere herein, embodiments of the present technology relate to infusing a diuretic and/or hydration fluid to increase or optimize urine output, and therein net fluid loss, from the patient. As previously described, standard treatment protocols can be ineffective for some patients that have unique conditions (e.g., low or high blood pressure, diuretic resistance), which can limit their maximum urine output rates and/or make treatment to achieve the maximum urine output rates more difficult. For such patients, different steps or protocols may be necessary to increase urine output and relieve fluid overload conditions.

The flowcharts shown and described with reference to FIGS. 3A-3C include protocols for improving fluid therapy, e.g., for the patients described above that have underlying conditions. As disclosed elsewhere herein, fluid therapy according to embodiments of the present technology can begin with the initial "dosage determining phase" to determine an appropriate diuretic dosage rate, and be followed by the "continuous delivery phase" in which the dosage rate is configured to maintain the patient's urine output at or above a desired urine output rate. The system 300 of FIGS. 3A and 3B can correspond to the continuous delivery phase. Referring to FIGS. 3A and 3B together, at the start of therapy the user (e.g., clinician, healthcare professional, patient, etc.) can be prompted to enter an amount of estimated excess fluid (process portion 301), which can establish a minimum goal for fluid removal during the therapy. Additionally or alternatively, the system 300 can prompt the user to enter one or more other inputs associated with patient fluid status. For example, the system 300 can prompt the user to enter a urine analyte and/or an amount thereof, an amount or percentage of fluid removed, a blood pressure, a level of creatinine and/or a change thereof, other physiological indicators and/or symptoms linked to heart failure, and/or other physiological parameters. Once the amount of estimated excess fluid and/or other physiological parameters are received by the system (e.g., the system 100), fluid therapy can begin by administering diuretic and/or hydration fluid. In some embodiments, the beginning of the fluid therapy corresponds to the "dose finding phase," as previously described with reference to FIGS. 1A and 2. Throughout the fluid therapy, the entered amount of estimated excess fluid can be compared to the actual fluid removed from the patient to determine a percentage of the amount of estimated excess fluid achieved and whether the goal is being met and/or expected to be met in a given time period. As described elsewhere herein, this percentage can be used by the system to determine whether sufficient or insufficient fluid loss has been achieved. In instances of insufficient fluid loss and/or a low urine output state, the system can determine one of more preferred subsequent actions. Such actions can include recommending a second diuretic be infused in addition to a first diuretic, and/or that an infused amount of hydration fluid (e.g., saline) be increased. Additionally or alternatively, this percentage can be used by the system to guide handling of a low urine output state after a high loop diuretic dose has been reached. In instances of low urine output prior to achieving a large percentage of removal of the amount of estimated excess fluid, the system can recommend and/or implement therapy escalation with the goal of increasing urine output. In instances of low urine output after achieving a large percentage of removal of the amount of estimated excess fluid, the system can recommend and/or implement therapy stoppage.

In some embodiments, the system may request the user update the amount of estimated excess fluid within a predetermined time (e.g., 12 hours, 18 hours, 24 hours, 26 hours, 29 hours, 30 hours, etc.) to have an updated estimate of the excess fluid to be removed from the patient. Before the predetermined time associated with the amount of estimated excess fluid lapses, the system may issue an alert indicating the amount of estimated excess fluid previously entered is about to expire, and repeatedly issue an alert (e.g., every hour) until the amount of estimated excess fluid is updated. After the predetermined time associated with the amount of estimated excess fluid lapses, the system can alert a user that the amount of estimated excess fluid is about to lapse. The system can determine whether the predetermined time associated with the amount of estimated excess fluid has elapsed after a time interval (e.g., every 5 minutes, 30 minutes, 1 hour, 2 hours, etc.). Once the amount of estimated excess fluid is updated, the timer for requesting an updated amount of estimated excess fluid is reset, and the system can continue to wait for a clinician or other user to update the amount of estimated excess fluid. Optionally, the patient's history (e.g., treatment history, fluid loss history, etc.) can be displayed once the amount of estimated excess fluid is updated. These prompts to request user input can also be applied to one or more other inputs associated with patient fluid status. For example, the system 300 can automatically measure or prompt the user to update a urine analyte and/or an amount thereof, an amount or percentage of fluid removed, a blood pressure, a level of creatinine and/or a change thereof, other physiological indicators and/or symptoms linked to heart failure, and/or other physiological parameters.

The system 300 can (e.g., after entering the amount of estimated excess fluid in process portion 301) reset a low urine rate timer and/or a urine debt ("debt") quantity or indicator (process portion 302), and/or update any measured and/or calculated values (process portion 304) associated with the system 300. As previously recited, the debt can correspond to the area on a plot between the urine output rate and a set rate, and can represent how much of and for how long the urine output rate has been below the set rate. Updating the measured/calculated values can include obtaining the patient's urine output rate, diuretic dosage rate, hydration fluid rate, and/or other data described herein. The system 300 can determine whether at least a portion the patient's therapy is scheduled to stop (process portion 306). If the system is scheduled to stop (process portion 306, "Yes"), the system 300 can stop the patient's therapy at a scheduled time (process portion 312). At the scheduled time (process portion 312, "Yes"), the system 300 can exit a continuous infusion phase and/or stop the delivery of diuretic(s) to the patient. Additionally or alternatively, a user may provide an input that causes the system 300 to exit a continuous infusion phase and/or stop the delivery of diuretic(s) to the patient. If it is not the scheduled time (process portion 312, "No"), the system 300 can wait a predetermined time period (e.g., at least one minute, two minutes, 10 minutes, 15 minutes, etc.) (process portion 324), and then update any measured and/or calculated values (process portion 304).

If the patient's therapy is not scheduled to stop (process portion 306, "No"), the system 300 can determine whether a treatment time period is greater than or equal to a low urine output check time (process portion 308). The low urine output check time can be at least 5 minutes, 10 minutes, 15 minutes, 20 minutes, 30 minutes, 1 hour, or another suitable time. If the treatment time period is less than the low urine output check time (process portion 308, "No"), the system 300 can compare a time since a reset of a low urine rate timer (e.g., process portion 302 and/or 340) to a predetermined urine rate check time (process portion 316; described in greater detail below), and if the treatment time period is greater than or equal to the low urine output check time (process portion 308, "Yes"), the system 300 can determine whether a urine output for a prior treatment time period (e.g., a treatment time period before the treatment time period in process portion 308) is greater than or equal to a low urine output threshold (process portion 310), e.g., before comparing the time since the reset of the low urine rate timer to the predetermined urine rate check time (process portion 316). The low output threshold can be at least 5 mL, 10 mL, 20 mL, 30 mL, 40 mL 50 mL, or another suitable urine output. If the urine output for the prior treatment time period is less than the low urine output threshold (e.g., if the urine output for the prior 15 minutes of treatment is less than 20 mL), the system 300 can provide an alert (e.g., to a user and/or via a status menu or display of the system 100) (process portion 314).

Whether the urine output for the prior treatment time period is less than, greater than, or equal to the low urine output threshold (process portion 310), the system 300 can compare the time since the reset of the low urine rate timer to the predetermined urine rate check time (process portion 316). The lower urine rate timer can be reset automatically, (e.g., in process portions 302 and/or 340) or by a user. The predetermined urine rate check time can be at least 5 minutes, 30 minutes, 1 hour, 2 hours, 3 hours, 6 hours, 12 hours, any amount of time therebetween, or another suitable amount of time. If the time since the reset of the low urine rate time is less than the predetermined urine rate check time (process portion 316, "No"), the system 300 can determine whether the patient meets one or more high output criteria (process portion 322). The high output criteria can include a urine output rate stop threshold (e.g., greater than 700 mL/hr, 800 mL/hr, 900 mL/hr, 1000 mL/hr, 1025 mL/hr, 1050 mL/hr, 1100 mL/hr, etc., for the past three hours or another time period), a urine output rate slope threshold (e.g., greater than 5 $ml/hr^2$, 10 $ml/hr^2$, 20 $ml/hr^2$, 30 $ml/hr^2$, 40 $ml/hr^2$, 50 $ml/hr^2$, 60 $ml/hr^2$, 70 $ml/hr^2$, etc., for the past 2 hours or another timer period), and/or a diuretic infusion rate threshold (e.g., greater than 5 mg/hr, 10 mg/hr, 15 mg/hr, 20 mg/hr, 30 mg/hr, 40 mg/hr, 50 mg/hr, etc.). If the patient does not meet one or more of the high output criteria (process portion 322, "No"), the system 300 can wait the predetermined time period (process portion 324), update any of the measured and/or calculated values (process portion 304), and/or repeat one or more process portion described herein. If the patient meets one or more of the high output criteria (process portion 322, "Yes"), the system 300 can set the patient's diuretic infusion rate to a proportion (e.g., up to 50%, 60%, 70%, 75%, 80%, 85%, 90%, 95%, or 99%) of the continuous infusion rate value (process portion 330) and exit continuous infusion to proceed to a down-titration phase or other phase described previously herein (e.g., with reference to FIG. 2).

If the time since the reset of the low urine rate time is greater than or equal to the predetermined urine rate check time (process portion 316, "Yes"), the system 300 can determine the urine output rate of the patient, such as an average urine output rate over a predetermined time (e.g., 3 hours) (process portion 318), and if the urine output rate is below a predetermined threshold ("predetermined urine output rate threshold") (e.g., at least 50 ml/hour, 100 mL/hour, 200 mL/hour, 300 mL/hour, 325 mL/hour, 400 mL/hour, etc.) (process portion 318, "Yes"), determine whether a diuretic infusion rate is less than a predetermined threshold ("predetermined diuretic rate") (e.g., at least 10 mg/hr, 20 mg/hr, 30 mg/hr, 40 mg/hr, etc.) (process portion 326). If a first diuretic (e.g., Lasix) has been infused below a predetermined or maximum rate ("predetermined diuretic rate) (e.g., 30 mg/hour)(process portion 326, "Yes"), the system 300 can recommend restarting the patient's ramp (e.g., initiating a re-ramp) (process portion 332) and wait the predetermined time period (process portion 324) before repeating one or more process portions of the system 300. In some embodiments, restarting the patient's ramp (process portion 332) can include restarting the dose finding, for example, by setting the diuretic delivery rate to a ramp corresponding to the continuous diuretic infusion rate, and exiting the continuous infusion phase to proceed to a dose finding phase. Dose finding can be restarted/re-initiated in response to an input from the user.

If the first diuretic has been infused at or above the predetermined diuretic rate (process portion 326, "No"), the system 300 can determine what percentage of the current amount of estimated excess fluid has actually been removed (process portion 334). If (i) more than a predetermined percentage (e.g., 60%, 70%, 80%, or 90%) of the amount of estimated excess fluid is removed (e.g., if a percent actual net fluid loss is greater than the predetermined percentage) or (ii) less than a predetermined volume ("predetermined fluid threshold") (e.g., 0.5 L, 0.8 L, 0.9 L, 1 L, 1.1 L, 1.2 L, or 1.5 L) is expected to remain in the patient (e.g., an amount of estimated fluid remaining or to be removed is greater than the predetermined fluid threshold) (process portion 334, "Yes"), the system 300 can generate an alert indicating that therapy will stop in a predetermined time (e.g., one hour) if no action is taken beforehand by the user (process portion 342), waiting the predetermined time period (process portion 324), and/or repeating one or more steps of the system 300. At this point, the user can (i) manually stop the therapy, (ii) determine whether the amount of estimated excess fluid should be increased, or (iii) extend the treatment for a period of time (e.g., by the predetermined urine rate check time). In some embodiments, the treatment may be extended if, for example, the user believes the urine output measured by the system is incorrect. If the user increases the amount of estimated excess fluid or the user extends the therapy, the timer for determining whether (i) the diuretic has been infused at or above the predetermined rate for the predetermined time and/or (ii) the urine output rate is above the predetermined urine output threshold for the predetermined urine rate check time is reset.

If the percentage of the amount of estimated excess fluid that has been removed is less than the predetermined percentage (e.g., less than 80%) and more than the predetermined volume of fluid remains (e.g., more than 1 L remains) (process portion 334, "No"), then the system 300 can attempt to increase urine production of the patient in a safe and efficient manner (e.g., as described herein with reference to FIG. 3C). For example, the system 300 can determine whether the amount of estimated excess fluid has been updated within a predetermined time (e.g., 24 hours, 30 hours, etc.) (process portion 336). If the amount of estimated excess fluid has not been updated within the predetermined time (process portion 336, "No"), an alert can be generated (process portion 338) indicating that the user needs to provide additional input, and that urine output of the patient is low. The system 300 can continue by resetting the low urine rate timer and the urine debt (process portion 340), and repeating one or more process portions of the system 300. If the amount of estimated excess fluid has been updated within the predetermined time (process portion 336, "Yes"), an alert can be generated indicating that the patient's urine output is low (process portion 344), and the system 300 can provide one or more outputs with recommendation(s) for adjusting the patient's urine output and/or cause one or more actions configured to adjust the patient's urine output ("process portion 346"; described in further detail with reference to FIG. 3C), reset the low urine rate timer and the urine debt (process portion 340), and repeat one or more process portions of the system 300.

If the urine output rate is at or above the predetermined urine output rate threshold (e.g., 325 mL/hour) (process portion 318, "No"), the system 300 can determine whether a urine debt of the patient is greater than a predetermined threshold ("urine debt threshold") (e.g., 150 mL), such as whether the patient's urine debt over a predetermined time (e.g., 3 hours) is less than the urine debt threshold (process portion 320). If the patient's urine debt is less than or equal to the urine debt threshold (process portion 320, "No"), the system 300 can determine whether the patient meets the one or more high output criteria (process portion 322), as described previously herein. If the patient's urine debt is greater than the urine debt threshold (process portion 320, "Yes), the system 300 can determine whether the diuretic infusion rate is less than the predetermined diuretic rate (process portion 328), which can be at least generally similar or identical to process portion 326, described previously herein. If the diuretic infusion rate is less than the predetermined diuretic rate (process portion 328, "Yes"), the system 300 can recommend restarting the patient's ramp (e.g., initiating a re-ramp) (process portion 332) and waiting the predetermined time period (process portion 324) before repeating one or more process portions of the system 300. If the diuretic infusion rate is equal to or greater than the predetermined diuretic rate (process portion 328, "No"), the system 300 can wait the predetermined time period (process portion 324) before repeating one or more process portions of the system 300.

FIG. 3C is a flow diagram for one or more actions (e.g., performed by the system 300) configured to adjust a patient's urine output (process portion 346), in accordance with embodiments of the present technology. The system 300 can determine whether a second diuretic (e.g., thiazide), in addition to the first diuretic, is currently being administered to the patient (process portion 350). If the second diuretic is not being administered (process portion 350, "No"), the system 300 can recommend doing so (process portion 354), e.g., via software or labeling. If the user agrees to administer the second diuretic (process portion 354, "Yes"), the system 300 can continue therapy (e.g., automatically and/or in response to user input) with both diuretics being administered by administering the second diuretic at a second diuretic infusion rate (process portion 360), clearing the low urine output alert (process portion 364), and returning to other process portions (e.g., process portion 340) of the system 300. In some embodiments, the system 300 can automatically administer the second diuretic (process portion 360). Although described as a second diuretic, a person of ordinary skill in the art will understand that process portion 360 can include, additionally or alternatively, administering one or more other drugs, pharmaceuticals, and/or compounds to the patient. In at least some embodiments, for example, process portion 360 includes administering a third diuretic (e.g., different than the first diuretic and/or the second diuretic) at a third dosage rate, administering a "nephron bomb" (e.g., loop diuretic, metolazone, spironolactone, acetazolamide, amiloride, and SGLT2i), performing ultrafiltration, performing continuous venovenous hemodialysis (CVVH), and/or another suitable therapeutic intervention. Alternatively, if the user does not agree to administer the second diuretic (process portion 354, "No"), e.g., because the patient has met other predetermined stopping criteria (e.g., low blood pressure, significant changes in electrolyte or creatinine levels, etc.) (process portion 356, "Yes"), then the user can be recommended to stop therapy and/or therapy can be stopped automatically or stopped automatically after a predetermined period of time has passed.

If the patient is already receiving the second diuretic (process portion 350, "Yes"), the system 300 can determine whether the patient is on increased fluid matching (process portion 352). If the patient is not on increased fluid matching (process portion 352, "No"), the system 300 may recommend increasing (e.g., temporarily increasing) infusion of the hydration fluid (e.g., saline) to match a higher rate (e.g., at least 80%, 90%, or 100%) of the urine output rate (process portion 358). If the user agrees to the increased hydration fluid match (process portion 358, "Yes"), the system 300 can continue therapy with the increased hydration fluid match (process portion 362), clearing the low urine output alert (process portion 364), and returning to the system 300 (e.g., process portion 340). In some embodiments, the system 300 can automatically continue therapy with the increased hydration fluid match (process portion 362). In these and other embodiments, the increased hydration fluid match may continue until (i) a predetermined volume (e.g., 500 mL) is matched, (ii) a predetermined amount of time elapses (e.g., 6 hours), or (iii) the measured urine output exceeds a predetermined threshold (e.g., 525 mL/hour). Additionally, or alternatively, the increased hydration fluid match (process portion 362) can include a single increase or multiple increases. For example, if after a first increase to the hydration fluid match (e.g., from 70% to 80%) the patient's urine output rate remains low, the system 300 can cause a second increase to the hydration fluid match (e.g., from 80% to 90%). If the user does not agree to the increased hydration fluid match (process portion 358, "No"), then the system 300 can recommend stopping therapy, for example, when the patient meets one or more stop criteria (process portion 356, "Yes") or, if the user feels the low urine output is incorrect, clear the alert and continue therapy as is (process portion 358, "No"; process portion 356, "No"; & process portion 364).

Although in FIG. 3C the system 300 is illustrated as determining whether the patient is on increased fluid matching (process portion 352) after determining whether the patient is on a second diuretic (process portion 350), in other embodiments the order of these process portions can be reversed. For example, the system 300 can determine whether the patient is on increased fluid matching (process portion 352) before determining whether the patient is on a second diuretic (process portion 350), and attempt to provide increased fluid matching prior to administering a second diuretic. Additionally, or alternatively, the system 300 can be configured to administer the second diuretic (process portion 360) and increase fluid matching (process portion 362) at the same time and/or independent of one another. That is, process portion 360 may not depend on whether process portion 362 altered the patient's urine output or had any effect, or vice versa. Alternatively, process portion 360 can be performed at some time delay (e.g., at least 1 minute, 5 minutes, 10 minutes, 30 minutes, 1 hour, 2 hours, 3 hours, etc.) after performing the process portion 362, or vice versa. For example, the system 300 can increase fluid matching (process portion 362) and, after 5 minutes, administer the second diuretic (process portion 360), e.g., without making a determination based on the patient's urine output and/or diuretic dosage rate(s).

As described with reference to FIGS. 3A-3C, embodiments of the present technology can advantageously manage a patient's urine output by ceasing fluid therapy for instances of sufficient fluid loss and improving fluid therapy by increasing urine output for instances of insufficient fluid loss. Moreover, for instances of insufficient fluid loss, the system can recommend actions to increase urine output that consider (i) the amount of estimated excess fluid entered by the user, (ii) the percentage of actual net fluid loss relative to the amount of estimated excess fluid, and (iii) the estimated fluid remaining in the patient, and thus is able to safely and effectively improve fluid therapy.

Figure 4:
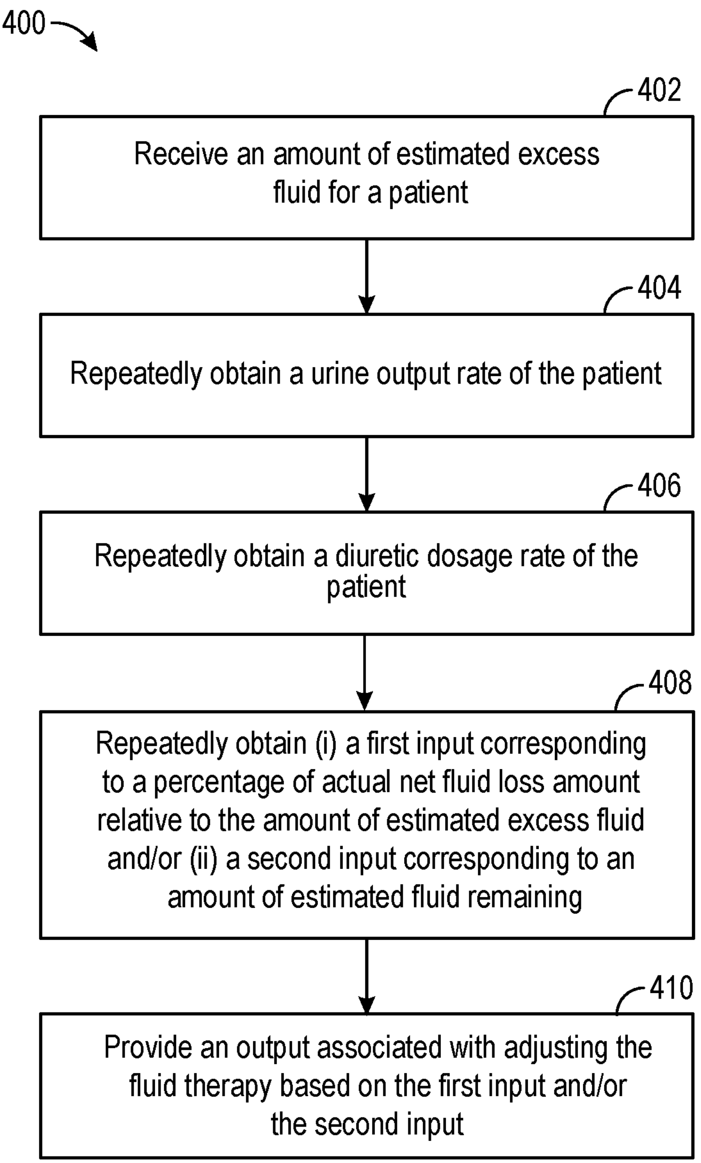
FIG. 4 is a flow diagram of a method for treating a patient, in accordance with embodiments of the present technology.

FIG. 4 is a flow diagram of a method 400 for providing fluid therapy to a patient. At least some aspects of the method 400 can be generally similar or identical to one or more aspects of the method 200 and/or be implemented by one or both of the systems 100, 300 described herein. The method 400 can include receiving an amount of estimated excess fluid for a patient (process portion 402), which as previously described can establish a goal for fluid removal during the therapy. The amount of estimated excess fluid can be automatically determined (e.g., based on the patient demographics, history of therapy treatment, current therapy treatment, etc.) and/or provided by a user (e.g., a physician, clinician, nurse, etc.), and can correspond to the amounts described with reference to process portion 301 (FIG. 3A).

The method 400 can include repeatedly obtaining a urine output rate of the patient (process portion 404), e.g., every second, 5 seconds, 30 seconds, 1 minutes, 5 minutes, 30 minutes, 1 hour, etc. This can be at least generally similar or identical to process portion 304 of the system 300. The urine output rate of the patient can be obtained using the controller 140 and/or urine system 110 of the system 100 of FIG. 1A. In some embodiments, other inputs may be obtained and used in addition to or in lieu of urine output rate. Such inputs can include urine analytes (type, concentration, change in concentration, etc.), blood pressure, creatinine (e.g., concentration, change in concentration, etc.), impedance measurements, clearance of tracers, and/or other physiological symptoms linked to heart failure.

The method 400 can include repeatedly obtaining a diuretic dosage rate of the patient (process portion 406), every second, 5 seconds, 30 seconds, 1 minutes, 5 minutes, 30 minutes, 1 hour, etc. This can be at least generally similar or identical to process portion 304 of the system 300. The diuretic dosage rate of the patient can be obtained using the controller 140 and/or the diuretic system 130 of the system 100 of FIG. 1A. In some embodiments, such as during the continuous delivery or infusion phase), the diuretic dosage rate may be relatively constant.

The method 400 can include repeatedly obtaining (i) a first input corresponding to a percentage of an actual net fluid loss amount relative to the amount of estimated excess fluid and/or (ii) a second input corresponding to an amount of estimated fluid remaining (process portion 408), every second, 5 seconds, 30 seconds, 1 minutes, 5 minutes, 30 minutes, 1 hour, etc. This can be at least generally similar or identical to process portion 304 of the system 300. The first input and/or the second input can be obtained using the controller 140 and/or the diuretic system 130 of the system 100 of FIG. 1A. For example, the first input can be obtained by dividing the actual net fluid loss amount by the amount of estimated excess fluid, and the second input can be determined based on the difference between the amount of fluid removed and the estimated of estimated excess fluid.

The method 400 can include providing an output associated with adjusting the fluid therapy based on the first input and/or the second input (process portion 410). In at least some embodiments, providing the output includes providing a recommendation or an indication with instructions to the user, e.g., via a display (e.g., the display 150 of FIG. 1A). The recommendation or instructions can be to use a different and/or additional diuretic to the patient, and/or to increase hydration fluid infusion to the patient.

In some embodiments, providing the output can comprise causing one or more actions configured to alter the urine output rate, e.g., based at least partially on the urine output rate, the diuretic dosage rate, the actual net fluid loss amount, and/or the amount of estimated fluid remaining. For example, the output can be configured to cause the urine output rate to be increased if the first input is below the predetermined percentage threshold, the second input is above a predetermined fluid threshold, or if both these conditions are met. The conditions of process portion 410 can be at least generally similar or identical to process portions 334 and/or 346 of the system 300. As such, the predetermined percentage threshold can be at least 60%, 70%, 80%, or 90% of the current amount of estimated excess fluid, and the predetermined fluid threshold can be 0.5 L, 0.8 L, 0.9 L, 1 L, 1.1 L, 1.2 L, or 1.5 L. When the first input or percentage of actual net fluid loss amount relative to the amount of estimated excess fluid is below the predetermined percentage threshold and the second input or amount of estimated fluid remaining is above the predetermined fluid threshold, then the action(s) configured to cause the urine output rate to be altered can include (i) recommending a second diuretic be infused to the patient and/or automatically infusing a second diuretic, and/or (ii) recommending fluid matching be increased and/or automatically infusing additional fluid to the patient. Administering a second diuretic can be at least generally similar or identical to process portions 334, 354, and/or 360 of the system 300. Fluid matching can be at least generally similar or identical to process portions 358 and/or 362 of the system 300. In some embodiments, recommending the second diuretic be infused, if applicable, occurs prior to recommending increased fluid matching. Alternatively, recommending the second diuretic be infused, if applicable, can occur after recommending increased fluid matching.

In some embodiments, such as when the first input is at or above the predetermined percentage threshold and/or the second input is below the predetermined fluid threshold, then providing the output (process portion 410) can include recommending that the patient's therapy be stopped, scheduling a time at which the patient's therapy will stop, and/or automatically stopping the patient's therapy. This can be at least generally similar or identical to process portion 334 and/or 342 of the system 300. Additionally or alternatively, the output can include one or more alerts or notifications provided to the user, such as an alert that the patient's urine output is low (process portion 344), and/or an alert that therapy will be stopped automatically (process portion 342), and/or an alert requesting the user's input (process portion 338), such as when the estimated excess fluid has not been updated with the predetermined update time (process portion 336, "NO").

Figure 5:
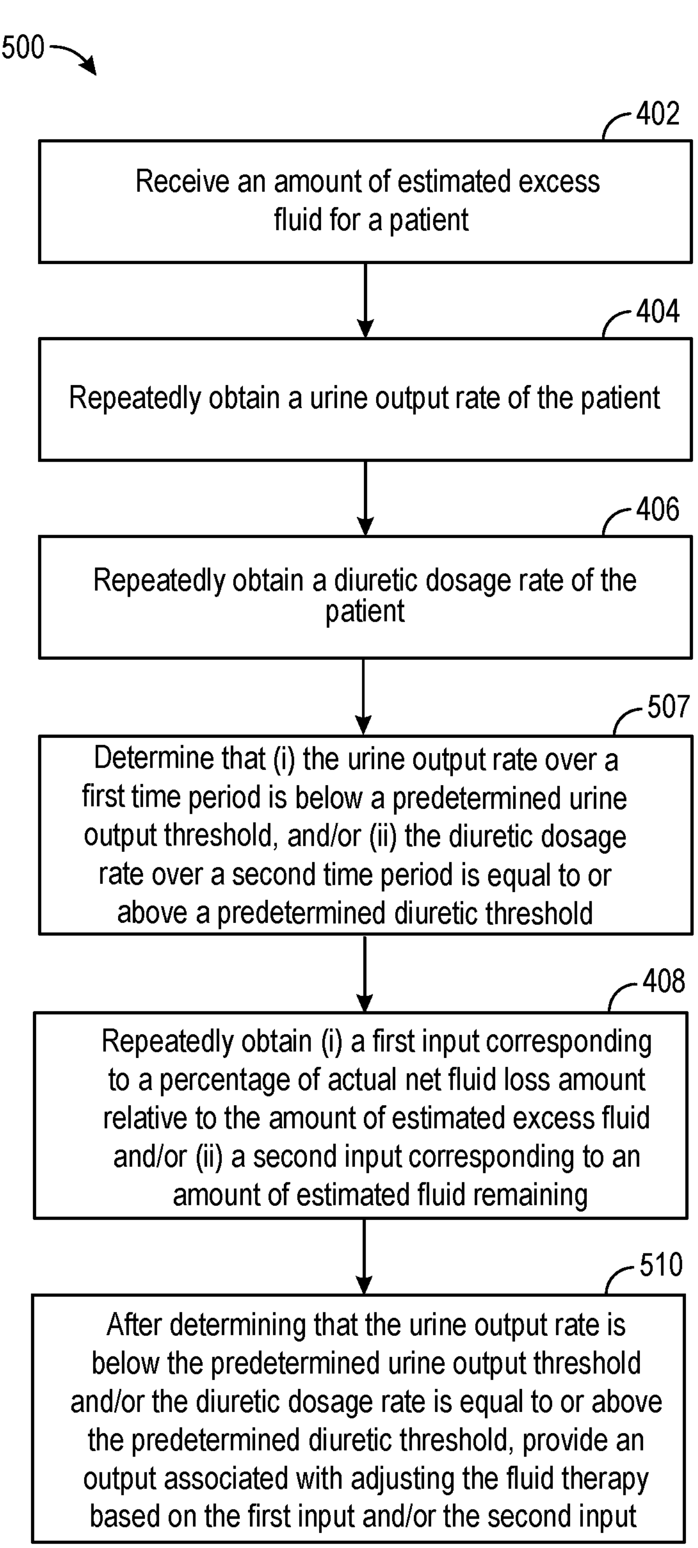
FIG. 5 is a flow diagram of another method for treating a patient, in accordance with embodiments of the present technology.

FIG. 5 is a flow diagram of a method 500 for providing fluid therapy to a patient. At least some aspects of the method 500 can be generally similar or identical to one or more aspects of one or both of the methods 200, 400 and/or be implemented by one or both of the systems 100, 300 described herein. For example, the method 500 can include process portions 402, 404, 406, and/or 408 of the method 400.

The method 500 can include determining whether (i) the urine output rate over a first time period is below a predetermined urine output threshold, and/or (ii) the diuretic dosage rate over a second time period is equal to or above a predetermined diuretic threshold. Determining whether the urine output rate over the first time period is below the predetermined urine output threshold can be at least generally similar or identical to process portion 318 of the system 300. For example, the predetermined urine output threshold can be at least 50 mL/hour, 100 mL/hour, 200 mL/hour, 300 mL/hour, 325 mL/hour, 400 mL/hour, etc., and/or the first time period can be the past one, two, or three hours. Determining whether the diuretic dosage rate over the second time period is equal to or above the predetermined diuretic threshold can be at least generally similar or identical to process portion 326 of the system 300. For example, the predetermined diuretic threshold can be at least 10 mg/hr, 20 mg/hr, 30 mg/hr, 40 mg/hr, etc., and/or the second time period can be the past one, two, or three hours.

The method 500 can include, after determining whether the urine output rate is below the predetermined urine output threshold and/or the diuretic dosage rate is equal to or above the predetermined diuretic threshold (process portion 507), providing an output associated with adjusting the fluid therapy based on the first input and/or the second input. Providing the output can be at least generally similar or identical to process portion 410 of the method 400. For example, providing the output can include adjusting the patient's urine output (process portion 346), providing one or more alerts (process portions 344, 338), and/or an output associated with stopping the patient's therapy (process portion 342). In some embodiments, providing the output only occurs if and/or when it is determined that the urine output rate is below the predetermined urine output threshold and the diuretic dosage rate is at or above the predetermined diuretic threshold. In such embodiments, if the urine output rate is not below the predetermined urine output threshold or the diuretic dosage rate is not equal to or above the predetermined diuretic threshold, the output may not be provided.

As outlined in methods 400 and 500 and elsewhere herein, embodiments of the present technology can determine whether a patient is experiencing insufficient fluid loss and make recommendations and/or take actions to improve fluid therapy. Before such recommendations and/or actions are made, aspects of the patient's current and previous therapy are considered to ensure any recommendations and/or actions are safe and warranted. For example, as described herein, such considerations can include the patient's (i) average urine output rate relative to a predetermined urine output threshold, (ii) average diuretic dosage rate relative to a predetermined diuretic threshold, (iii) a percentage of actual net fluid loss relative to an amount of estimated excess fluid, and/or (iv) an amount of estimated fluid remaining. Advantageously, embodiments of the present technology are able to provide fluid therapy while also considering other safety concerns, such as the risk of hypotension to the patient. As previously described, the risk of hypotension can be directly correlated to treatment effectiveness, and thus must be considered as adjustments to therapy are made or recommended. By considering the conditions (i)—(iv) above, or more specifically by recommending certain actions (e.g., administering an additional diuretic and/or increasing hydration fluid infusion rates) only after certain of the conditions (i)—(iv) are met, embodiments of the present technology are able to balance safety (e.g., the risk of hypotension) against effectiveness throughout therapy. In doing so, a more optimal fluid therapy can be provided for patients.

III. Conclusion

The present technology is illustrated, for example, according to various aspects described below. Various examples of aspects of the present technology are described as numbered examples (1, 2, 3, etc.) for convenience. These are provided as examples and do not limit the present technology. It is noted that any of the dependent examples may be combined in any combination, and placed into a respective independent example. The other examples can be presented in a similar manner.

EXAMPLES

1. A method for providing fluid therapy, the method comprising:
   - receiving an estimated amount of excess fluid for a patient;
   - repeatedly obtaining a urine output rate of the patient;
   - repeatedly obtaining a diuretic dosage rate of the patient;
   - determining whether (i) the urine output rate over a first time period is below a predetermined urine output threshold, and/or (ii) the diuretic dosage rate over a second time period is above a predetermined diuretic threshold;
   - repeatedly obtaining (i) a first input corresponding to a percentage of an actual amount of net fluid loss relative to the estimated amount of excess fluid, and/or (ii) a second input corresponding to an estimated amount of fluid remaining; and
   - after determining whether the urine output rate is below the predetermined urine output threshold and/or the diuretic dosage rate is at or above the predetermined diuretic threshold, providing an output associated with adjusting the fluid therapy based on the first input and/or the second input.

2. The method of example 1, wherein providing the output comprises providing an indication with instructions to use a different diuretic and/or increase an amount of hydration fluid provided to the patient.

3. The method of example 1 or example 2, wherein the diuretic dosage rate is for a first diuretic, and wherein providing the output comprises providing an indication with instructions to provide a second diuretic to the patient.

4. The method of example 3, wherein the first diuretic comprises bumetanide, ethacrynic acid, furosemide, and/or torsemide, and wherein the second diuretic is different than the first diuretic and comprises bumetanide, ethacrynic acid, furosemide, torsemide, a thiazide-type diuretic, chlorothiazide, metolazone, amiloride, or spironolactone.

5. The method of any of examples 1-4, further comprising providing a hydration fluid to the patient at a first rate, and wherein providing the output comprises recommending providing or providing the hydration fluid to the patient at a second rate higher than the first rate.

6. The method of any of examples 1-5, wherein, when the first input is above a predetermined percentage threshold or the second input is below the predetermined fluid threshold, providing the output comprises providing an indication with instructions to decrease the diuretic dosage rate and/or a hydration fluid infusion rate.

7. The method of any of examples 1-6, wherein the first time period is at least 1 hour, and the predetermined urine output threshold is at least 325 milliliters/hour.

8. The method of any of examples 1-7, wherein the second time period is at least 1 hour, and the predetermined diuretic threshold is at least 30 milligrams/hour.

9. The method of any of examples 1-8, wherein providing the output occurs only if the first input is below a first threshold and the second input is above a second threshold.

10. A fluid therapy system, comprising:
    - a urine measurement device configured to repeatedly measure urine output from a patient at predetermined intervals;

a pump configured to provide a diuretic to the patient at a diuretic dosage rate;

one or more processors; and tangible, non-transitory computer-readable media having instructions that, when executed by the one or more processors, cause the fluid therapy system to perform operations comprising— receiving an estimated amount of excess fluid for the patient;

obtaining a urine output rate of the patient;

obtaining a diuretic dosage rate of the patient;

obtaining (i) a first input corresponding to a percentage of an actual amount of net fluid loss relative to the estimated amount of excess fluid, and/or (ii) a second input corresponding to an estimated amount of fluid remaining; and based on the first input and/or the second input, providing an output associated with adjusting the fluid therapy.

11. The system of example 10, wherein providing the output comprises providing instructions to use a different diuretic and/or increase an amount of hydration fluid provided to the patient.

12. The system of example 10 or example 11, wherein the diuretic is a first diuretic, the system further comprising a second pump configured to provide a second diuretic different than the first diuretic, wherein providing the output comprises providing instructions to infuse the second diuretic to the patient via the second pump.

13. The system of any of examples 10-12, wherein the pump is a first pump, the system further comprising a second pump configured to infuse a hydration fluid to the patient at a first rate, and wherein providing the output comprises providing instructions to infuse the hydration fluid to the patient at a second rate higher than the first rate.

14. The system of any of examples 10-13, wherein, when the first input is above a predetermined percentage threshold or the second input is below the predetermined fluid threshold, providing the output comprises providing instructions to decrease the diuretic dosage rate and/or a hydration fluid infusion rate.

15. The system of any of examples 10-14, further comprising determining that the urine output rate over a time period is below a predetermined urine output threshold, and wherein providing the output occurs after determining that the urine output rate is below the predetermined urine output threshold.

16. The system of example 15 wherein the predetermined urine output threshold is at least 325 milliliters/hour.

17. The system of any of examples 10-16, further comprising determining that the diuretic dosage rate over a time period is equal to or above a predetermined diuretic threshold, and wherein providing the output occurs after determining that the urine output rate is below the predetermined urine output threshold.

18. The system of example 17, wherein the predetermined diuretic threshold is at least 30 milligrams/hour.

19. Tangible, non-transitory computer-readable media having instructions that, when executed by one or more processors, cause a fluid therapy system to perform operations comprising:

receiving an estimated amount of excess fluid for a patient;

determining whether a urine output rate of the patient over a first time period is below a predetermined urine output threshold;

determining whether a diuretic dosage rate of the patient over a second time period is equal to or above a predetermined diuretic threshold; and when the urine output rate is at or below the predetermined urine output threshold and the diuretic dosage rate is at or above the predetermine diuretic threshold, providing an output associated with adjusting the fluid therapy to the patient, wherein the output includes instructions to (i) administer an additional diuretic to the patient and/or (ii) increase infusion of a hydration fluid to the patient.

20. The computer-readable media of example 19, wherein the operations further comprise obtaining an input corresponding to a percentage of an actual amount of net fluid loss relative to the estimated amount of excess fluid, and wherein providing the output is further based on the input.

21. The computer-readable media of example 19 or example 20, wherein the operations further comprise obtaining an input corresponding to an estimated amount of fluid remaining in the patient, and wherein providing the output is further based on the input.

22. The computer-readable media of any of examples 19-21, wherein the operations further comprise obtaining (i) a first input corresponding to a percentage of an actual amount of net fluid loss relative to the estimated amount of excess fluid, and/or (ii) a second input corresponding to an estimated amount of fluid remaining, and wherein providing the output is further based on the first input and the second input.

23. The computer-readable media of example 22, wherein providing the output occurs only if the first input is below a first threshold and the second input is above a second threshold.

24. The computer-readable media of example 22 or example 23, wherein the output is a first output, the computer-readable media further comprising, when the first input is above the predetermined percentage threshold and/or the second input is below the predetermined fluid threshold, providing a second output including instructions to decrease the diuretic dosage rate and/or a hydration fluid infusion rate.

25. The computer-readable media of any of examples 19-24, wherein the first time period is at least 1 hour and the predetermined urine output threshold is at least 325 milliliters/hour.

26. The computer-readable media of any of examples 19-25, wherein the second time period is at least 1 hour and the predetermined diuretic threshold is at least 30 milligrams/hour.

27. A method for providing fluid therapy, the method comprising:

receiving an amount of estimated excess fluid for a patient;

repeatedly obtaining a urine output rate of the patient;

repeatedly obtaining a diuretic dosage rate of the patient repeatedly obtaining a percentage of actual net fluid loss amount relative to the amount of estimated excess fluid; and causing an action configured to alter the urine output rate based at least partially on the urine output rate, the diuretic dosage rate, and at least one of (i) the percentage relative to a predetermined percentage threshold, or (ii) an amount of estimated fluid remaining relative to a predetermined fluid threshold.

28. The method of example 27 wherein repeatedly obtaining the urine output rate of the patient includes repeatedly obtaining the urine output rate of the patient at a first predetermined interval, and/or wherein repeatedly obtaining the diuretic dosage rate of the patient includes repeatedly obtaining the diuretic dosage rate of the patient at a second predetermined interval.

29. The method of example 28 wherein the first predetermined interval and the second predetermined interval are a same predetermined interval.

30. The method of any of examples 27-29, wherein the diuretic dosage rate is for a first diuretic to be infused into the patient, and wherein, when the percentage is below the predetermined percentage threshold and the amount of estimated excess fluid remaining is above the predetermined fluid threshold, the action comprises causing a second diuretic be infused to the patient.

31. The method of any of example 30, wherein the first diuretic comprises bumetanide, ethacrynic acid, furosemide, torsemide, or thiazide, and the second diuretic is different than the first diuretic.

32. The method of any of examples 27-31, further comprising infusing a hydration fluid to the patient at a first rate, wherein, when the percentage is below the predetermined percentage threshold and the amount of estimated excess fluid remaining is above the predetermined fluid threshold, the action comprises causing the hydration fluid to be infused at a second rate higher than the first rate.

33. The method of any of examples 27-32, wherein the percentage is below the predetermined percentage threshold and the amount of estimated fluid remaining is above the predetermined fluid threshold, wherein the diuretic dosage rate is for a first diuretic being infused into the patient, and wherein the action comprises causing (i) a second diuretic to be infused into the patient and (ii) increased infusion of hydration fluid to the patient.

34. The method of any of examples 27-33 wherein, when the percentage is above the predetermined percentage threshold or the amount of estimated fluid remaining is below the predetermined fluid threshold, and wherein the action comprises causing at least one of the diuretic or the hydration fluid to stop being delivered to the patient.

35. The method of any of examples 27-34 wherein causing the action is further based on the urine output rate being less than a predetermined urine output threshold.

36. The method of example 35 wherein comparing the urine output rate to the predetermined urine output threshold includes comparing an average urine output rate over a predetermined urine rate check time to the predetermined urine output threshold.

37. The method of example 36 wherein the predetermined urine rate check time is at least 1 hour, and wherein the predetermined urine output threshold is at least 325 milliliters/hour.

38. The method of any of examples 27-37 wherein causing the action is further based on the diuretic dosage rate being at or above a predetermined diuretic dosage rate.

39. The method of example 38 wherein comparing the diuretic dosage rate to the predetermined diuretic rate includes comparing the diuretic dosage rate to the predetermined diuretic dosage rate over a predetermined urine rate check time.

40. The method of example 39 wherein causing the action includes causing the action when the diuretic dosage rate is at or above the predetermined diuretic dosage rate for the predetermined urine rate check time.

41. The method of example 39 or example 40 wherein the predetermined urine rate check time is at least 1 hour, and wherein the predetermined diuretic dosage rate is at least 30 milligrams/hour.

42. The method of any of examples 27-41, further comprising setting a delivery stop time for at least one of a diuretic or a hydration fluid when (i) the percentage of actual net fluid loss amount relative to the target net fluid loss amount is below the predetermined percentage, and/or (ii) the estimated amount of fluid to be removed is below the predetermined fluid threshold.

43. A fluid therapy system, comprising:

a urine measurement device configured to repeatedly measure urine output from a patient at predetermined intervals;

a pump configured to provide a diuretic to the patient at a diuretic dosage rate;

one or more processors; and tangible, non-transitory computer-readable media having instructions that, when executed by the one or more processors, cause the fluid therapy system to perform operations comprising— receiving an amount of estimated excess fluid for the patient;

obtain a percentage of actual net fluid loss amount relative to the amount of estimated excess fluid;

obtain an amount of estimated fluid remaining from the patient; and causing an action configured to alter the urine output rate based on at least one of (i) the percentage relative to a predetermined percentage threshold, or (ii) the amount of estimated fluid remaining relative to a predetermined fluid threshold.

44. The system of example 43 wherein the diuretic dosage rate is for a first diuretic to be infused into the patient, and wherein, when the percentage is below a predetermined percentage threshold and the amount of estimated fluid remaining is above the predetermined fluid threshold, causing the action comprises causing a second diuretic to be infused to the patient.

45. The system of example 43 or example 44, wherein the operations further comprise infusing a hydration fluid into the patient.

46. The system of example 45 wherein the hydration fluid is infused into the patient at a first rate, wherein, when the percentage is below a predetermined percentage threshold and the amount of estimated fluid remaining is above the predetermined fluid threshold, causing the action comprises recommending causing the hydration fluid to be infused at a second rate higher than the first rate.

47. The system of any of examples 43-46, wherein the percentage is below a predetermined percentage threshold and the amount of estimated fluid remaining is above the predetermined fluid threshold, wherein the diuretic is a first diuretic, and wherein causing the action comprises causing (i) a second diuretic to be infused to the patient and (ii) increasing an infusion rate of the hydration fluid to the patient.

48. The system of any of examples 43-47 wherein, when the percentage is above a predetermined percentage threshold or the amount of estimated fluid remaining is below the predetermined fluid threshold, causing the action comprises causing at least one of the diuretic or the hydration fluid to stop being delivered to the patient.

49. The system of any of examples 43-48 wherein causing the action is further based on the urine output rate being less than a predetermined urine output threshold.

50. The system of example 49 wherein the operations further comprise comparing an average urine output rate over a predetermined urine rate check time to the predetermined urine output threshold.

51. The system of example 50 wherein the predetermined urine rate check time is at least 3 hours, and wherein the predetermined urine output threshold is at least 325 milliliters/hour.

52. The system of any of examples 43-51 wherein causing the action is further based on the diuretic dosage rate being at or above a predetermined diuretic dosage rate.

53. The system of example 52 wherein the operations further comprise comparing the diuretic dosage rate to the predetermined diuretic dosage rate over a predetermined urine rate check time.

54. The system of example 53 wherein causing the action includes causing the action when the diuretic dosage rate is at or above the predetermined diuretic dosage rate for the predetermined urine rate check time.

55. The system of example 53 or example 54 wherein the predetermined urine rate check time is 3 hours, and wherein the predetermined diuretic dosage rate is at least 30 milligrams/hour.

56. A method for providing fluid therapy, the method comprising:

- receiving a low urine output indication for a patient, wherein receiving the low urine output indication includes at least one of—
  - determining that a percentage of actual net fluid loss amount relative to an amount of estimated excess fluid is above a predetermined percentage, or
  - determining that an amount of estimated excess fluid remaining is above a predetermined fluid threshold; and
- based on the received low urine output indication, causing an action configured to increase a urine output of the patient by—
  - administering a diuretic to the patient at a diuretic infusion rate, and/or
  - increasing infusion of a hydration fluid into the patient.

57. The method of example 56 wherein causing the action includes increasing a rate of hydration fluid infusion to the patient.

58. The method of example 56, further comprising administering a first diuretic to the patient, wherein causing the action includes administering a second diuretic to the patient.

59. The method of any of examples 56-58 wherein the predetermined percentage is at least 80% and the predetermined fluid threshold is at least 1 Liter.

60. The method of any of examples 56-59 wherein administering the diuretic includes automatically administering, via a fluid therapy system, the diuretic to the patient.

61. The method of any of examples 56-60 wherein increasing infusion of the hydration fluid includes automatically increasing, via a fluid therapy system, infusion of the hydration fluid.

62. A method for providing fluid therapy, the method comprising:

- receiving an amount of estimated excess fluid for a patient;
- obtaining a percentage of an actual net fluid loss amount relative to the amount of estimated excess fluid;
- obtaining an estimated amount of excess fluid to be removed; and
- causing an action configured to alter a urine output rate of the patient based on at least one of (i) the percentage being above a predetermined percentage threshold, or (ii) the estimated amount of fluid being above a predetermined fluid threshold.

It will be apparent to those having skill in the art that changes may be made to the details of the above-described embodiments without departing from the underlying principles of the present technology. In some cases, well known structures and functions have not been shown or described in detail to avoid unnecessarily obscuring the description of the embodiments of the present technology. Although steps of methods may be presented herein in a particular order, alternative embodiments may perform the steps in a different order. Similarly, certain aspects of the present technology disclosed in the context of particular embodiments can be combined or eliminated in other embodiments. Furthermore, while advantages associated with certain embodiments of the present technology may have been disclosed in the context of those embodiments, other embodiments can also exhibit such advantages, and not all embodiments need necessarily exhibit such advantages or other advantages disclosed herein to fall within the scope of the technology. Accordingly, the disclosure and associated technology can encompass other embodiments not expressly shown or described herein, and the invention is not limited except as by the appended claims.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising," "including," and "having" should be interpreted to mean including at least the recited feature(s) such that any greater number of the same feature and/or additional types of other features are not precluded.

Reference herein to "one embodiment," "an embodiment," "some embodiments" or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

Unless otherwise indicated, all numbers expressing concentrations, shear strength, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present technology. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10, i.e., any and all subranges having a minimum value of equal to or greater than 1 and a maximum value of equal to or less than 10, e.g., 5.5 to 10.

The disclosure set forth above is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

We claim:

1. A fluid therapy system, comprising:

a urine measurement device configured to repeatedly measure urine output from a patient at predetermined intervals;

one or more pumps configured to provide a diuretic to the patient at a diuretic dosage rate, to provide a hydration fluid to the patient at a hydration fluid rate, and/or to provide a different diuretic to the patient;

one or more processors; and tangible, non-transitory computer-readable media having instructions that, when executed by the one or more processors, cause the fluid therapy system to perform operations comprising— receiving an estimated amount of excess fluid for the patient;

obtaining a urine output rate of the patient;

obtaining a diuretic dosage rate of the patient;

determining that (i) the urine output rate over a first time period of at least one hour is below a predetermined urine output threshold and (ii) the diuretic dosage rate over a second time period of at least one hour is equal to or above a predetermined diuretic threshold of at least 5 milligrams/hour;

obtaining (i) a first input corresponding to a percentage of an actual amount of net fluid loss relative to the estimated amount of excess fluid, and/or (ii) a second input corresponding to an estimated amount of excess fluid remaining; and based on (i) the urine output rate being below the predetermined urine output threshold for the first time period, (ii) the diuretic dosage rate being equal to or above a predetermined diuretic threshold for the second time period, and (iii) the first input and/or the second input, providing an output associated with adjusting fluid therapy provided to the patient, wherein providing the output comprises (i) adjusting the diuretic dosage rate of the the diuretic via the one or more pumps, (ii) infusing a hydration fluid to the patient via the one or more pumps, and/or (iii) administering the different diuretic to the patient via the one or more pumps.

2. The fluid therapy system of claim 1, wherein providing the output comprises providing instructions to (i) adjust the diuretic dosage rate of the diuretic, (ii) adjust the amount of hydration fluid provided to the patient, (iii) administer the different diuretic to the patient.

3. The fluid therapy system of claim 1, wherein the diuretic is a first diuretic administered to the patient via a first one of the one or more pumps, and wherein providing the output comprises providing instructions to infuse the different diuretic to the patient via a second one of the one or more pumps.

4. The fluid therapy system of claim 1, wherein the one or more pumps comprise a hydration fluid pump configured to infuse the hydration fluid to the patient at a first rate, and wherein providing the output comprises infusing the hydration fluid to the patient via the hydration fluid pump at a second rate higher than the first rate.

5. The fluid therapy system of claim 1, wherein, when the first input is above a predetermined percentage threshold or the second input is below a predetermined fluid threshold, providing the output comprises providing instructions to decrease the diuretic dosage rate and/or a hydration fluid infusion rate.

6. The fluid therapy system of claim 1, wherein the predetermined urine output threshold is at least 325 milliliters/hour.

7. The fluid therapy system of claim 1, wherein the predetermined diuretic threshold is at least 30 milligrams/hour.

8. A fluid therapy system, comprising:

tangible, non-transitory computer-readable media having instructions that, when executed by one or more processors, cause the fluid therapy system to perform operations comprising— receiving an estimated amount of excess fluid for the patient;

obtaining a urine output rate of the patient;

obtaining a diuretic dosage rate of the patient;

determining that (i) the urine output rate over a first time period of at least one hour is below a predetermined urine output threshold and (ii) the diuretic dosage rate over a second time period of at least one hour is equal to or above a predetermined diuretic threshold of at least 5 milligrams/hour;

obtaining (i) a first input corresponding to a percentage of an actual amount of net fluid loss relative to the estimated amount of excess fluid, and/or (ii) a second input corresponding to an estimated amount of excess fluid remaining; and based on the urine output rate being below the predetermined urine output threshold for the first time period, and the diuretic dosage rate being equal to or above a predetermined diuretic threshold for the second time period input, and the first input and/or the second input, providing an output associated with adjusting fluid therapy provided to the patient, wherein providing the output comprises (i) adjusting the diuretic dosage rate of the the diuretic via one or more pumps, (ii) infusing a hydration fluid to the patient via one or more pumps, and/or (iii) administering a different diuretic to the patient via one or more pumps.

9. The fluid therapy system of claim 8, wherein the predetermined urine output threshold is at least 325 milliliters/hour.

10. The fluid therapy system of claim 8, wherein the predetermined diuretic threshold is at least 30 milligrams/hour.

11. The fluid therapy system of claim 8, wherein providing the output comprises providing instructions to (i) adjust the diuretic dosage rate of the diuretic, (ii) adjust the amount of hydration fluid provided to the patient, (iii) administer the different diuretic to the patient.

* * * * *